US009283391B2

United States Patent
Ahmed

(10) Patent No.: US 9,283,391 B2
(45) Date of Patent: Mar. 15, 2016

(54) TRANS-SPINAL DIRECT CURRENT MODULATION SYSTEMS

(71) Applicant: Zaghloul Ahmed, Staten Island, NY (US)

(72) Inventor: Zaghloul Ahmed, Staten Island, NY (US)

(73) Assignee: The Research Foundation of the City University of New York, New York, NY (US)

( * ) Notice: Subject to any disclaimer, the term of this patent is extended or adjusted under 35 U.S.C. 154(b) by 0 days.

(21) Appl. No.: 14/579,829

(22) Filed: Dec. 22, 2014

(65) Prior Publication Data

US 2015/0196767 A1    Jul. 16, 2015

Related U.S. Application Data

(60) Provisional application No. 61/919,806, filed on Dec. 22, 2013, provisional application No. 61/925,423, filed on Jan. 9, 2014, provisional application No. 62/092,214, filed on Dec. 15, 2014.

(51) Int. Cl.
   *A61N 1/36*   (2006.01)
   *A61N 1/05*   (2006.01)
   *A61N 1/20*   (2006.01)

(52) U.S. Cl.
   CPC .............. *A61N 1/36157* (2013.01); *A61N 1/20* (2013.01); *A61N 1/205* (2013.01); *A61N 1/0551* (2013.01)

(58) Field of Classification Search
   CPC ............ A61N 1/36157; A61N 1/0551; A61N 1/36003; A61N 1/36007
   See application file for complete search history.

(56) References Cited

U.S. PATENT DOCUMENTS

| | | | |
|---|---|---|---|
| 6,366,814 B1 * | 4/2002 | Boveja et al. | 607/45 |
| 2004/0210261 A1 | 10/2004 | King et al. | |
| 2006/0052826 A1 * | 3/2006 | Kim et al. | 607/2 |
| 2006/0122660 A1 * | 6/2006 | Boveja et al. | 607/40 |
| 2007/0073357 A1 | 3/2007 | Rooney et al. | |
| 2008/0071321 A1 * | 3/2008 | Boggs et al. | 607/39 |
| 2013/0053922 A1 * | 2/2013 | Ahmed et al. | 607/45 |
| 2013/0072998 A1 | 3/2013 | Su et al. | |
| 2013/0261696 A1 | 10/2013 | Thacker et al. | |
| 2014/0180361 A1 * | 6/2014 | Burdick et al. | 607/49 |
| 2015/0073232 A1 * | 3/2015 | Ahmad et al. | 600/301 |

* cited by examiner

*Primary Examiner* — Catherine Voorhees
(74) *Attorney, Agent, or Firm* — Burns & Levinson LLP; Orlando Lopez

(57) ABSTRACT

Improved neuromodulation control of neurological abnormalities associated with effector organs in vertebrate beings using direct current stimulation for modulating spinal cord excitability, having a peripheral-current supplying component for providing direct current peripheral nerve stimulation and a spinal-current supplying component providing direct current for spinal stimulation, and a controller managing such functions.

29 Claims, 24 Drawing Sheets

TRANS-SPINAL DIRECT CURRENT MODULATION SYSTEMS

CROSS-REFERENCE TO RELATED APPLICATIONS

Priority is claimed upon U.S. Provisional Application Ser. No. 62/092,214, filed Dec. 15, 2014, entitled: Trans-spinal Direct Current Stimulation Systems, U.S. Provisional Application Ser. No. 61/925,423, flied Jan. 9, 2014, entitled: Method and Apparatus for Safe Regulation of Muscle Tone, and U.S. Provisional Application Ser. No. 61/919,806, filed Dec. 22, 2013, entitled: Method and Apparatus for Regulation of Muscle Tone. All of the foregoing are incorporated herein by reference in their entirety for all purposes whatsoever.

FIELD

The present invention relates to method and apparatus for modulating spinal cord excitability for regulation of effector organs, such as regulation of muscle tone and regulation of autonomic system functions.

BACKGROUND

The nervous system includes the Central Nervous System (CNS) and the Peripheral Nervous System (PNS), the latter including the Somatic Nervous System (SNS) and Autonomic Nervous System (ANS). The CNS includes the brain and the spinal cord. The spinal cord is the main communication route for signals between the body and the brain. The PNS carries signals outside the brain and spinal cord throughout the rest of the body, including carrying motor signals to muscles and carrying sending feedback to the brain, including touch and pain signals from the skin. The SNS and ANS overlap the CNS and PNS. There are 31 pairs of spinal nerves arising from cervical (8), thoracic (12), lumbar (5), sacral (15) and coccygeal (1) segments. The spinal nerves contain both sensory and motor fibers. Efferent nerves (as opposed to afferent nerves) are the nerves leading from the central nervous system to an effector organ, and efferent neural outflow refers to neural signals from the brain that are transmitted via spinal cord pathways to effector organs.

The SNS is the part of the peripheral nervous system associated with the voluntary control of movement via the Skeletal muscles. The ANS consists of two divisions, the sympathetic nervous system and the parasympathetic nervous system, and is responsible for regulating bodily functions including heart rate, respiration, digestion, bladder tone, sexual response and other functions. Activation of the sympathetic nervous system results in preparation of the body for stressful or emergency situations, while activation of the parasympathetic nervous system results in conservation and restoration and controls body processes during normal situations. The autonomic nervous system includes both sensory and motor neurons. Preganglionic neurons start in the CNS and project to a ganglion in the body where they connect with postganglionic neurons that connect with a specific organ.

There are many disorders and dysfunctions associated with abnormal regulation of effector organs, which may be due to disturbances in any component of the nervous system. These effector organs can be skeletal muscles under voluntary control, smooth muscle under autonomic control, or visceral organs and glands. We have developed a novel approach to modulating these systems using trans-spinal direct current stimulation (tsDCS).

Muscle tone abnormalities are associated with many neurological pathologies and can severely limit motor function and control. Muscle tone depends on the level of excitability of spinal motoneurons and interneurons. Muscle tone abnormalities can be due to either decreased tone (hypotonus) or increased tone (hypertonus). Hypotonia is commonly observed, for example, in patients with cerebellar deficits and spinocerebellar lesions and in developmentally-delayed children, including those with Down's syndrome. Hypertonia is commonly observed, for example, in patients with cerebral palsy, stroke, spinal cord injury (SCI), brain injury, multiple sclerosis and numerous other neurological disorders. Hypertonia includes spasticity and rigidity and is characterized by a velocity-dependent increase in tonic stretch reflexes and increased muscle activity during passive stretch. Spasticity can range from mild to severe and can cause striking impairments in functional movement. There is a long felt need for better ability to control and regulate muscle tone. Spinal cord injury is one indication where an increase in muscle tone is often seen.

Increases in reflex excitability following SCI may be caused by a number of factors, including increased excitability of spinal motoneurons and changes in interneuronal physiology and connectivity. In general, following SCI, increased excitation and reduced inhibition of the mechanisms controlling motoneurons causes abnormal generation of force, resulting in spasticity. Pharmacological, surgical, and physical treatments to manage spasticity have at best short-term efficacy and are confounded by side effects.

Beyond skeletal muscle disorders, there are numerous disorders related to dysfunction of either the sympathetic or parasympathetic system that have been described. These ANS disorders are referred to as dysautonomias, and can be due to failure or disruption of either the sympathetic or parasympathetic divisions of the ANS. Specific such disorders include familial dysautonomia, autoimmune autonomic ganglionopathy, congenital central hypoventilation syndrome, Holmes-Adie syndrome, multiple system atrophy, Shy-Drager syndrome, neurally mediated syncope, orthostatic hypotension, postural tachycardia syndrome, striatonigral degeneration and vasovagal syncope. No effective treatments currently exist for these dysautonomias. A novel approach to autonomic neuromodulation would not only open new treatment options for these patients, but would enable the harnessing of the autonomic nervous system to modulate the activity of all the organ systems innervated autonomically.

There remains a need for improved method and apparatus for neuromodulation and regulation of effector organs.

SUMMARY

In one or more embodiments, the method of these teachings includes applying a source of electrical stimulation along a nerve that provides neural control of a target effector organ and applying a source of direct current to a spinal location associated with efferent neural outflow to the target effector organ.

A number of other embodiments including a number of methods of use are also disclosed.

BRIEF DESCRIPTION OF THE DRAWINGS

The above illustrative and further embodiments are described below in conjunction with the following drawings, where specifically numbered components are described and will be appreciated to be thus described in all figures of the disclosure.

DETAILED DESCRIPTION

Figure 1:
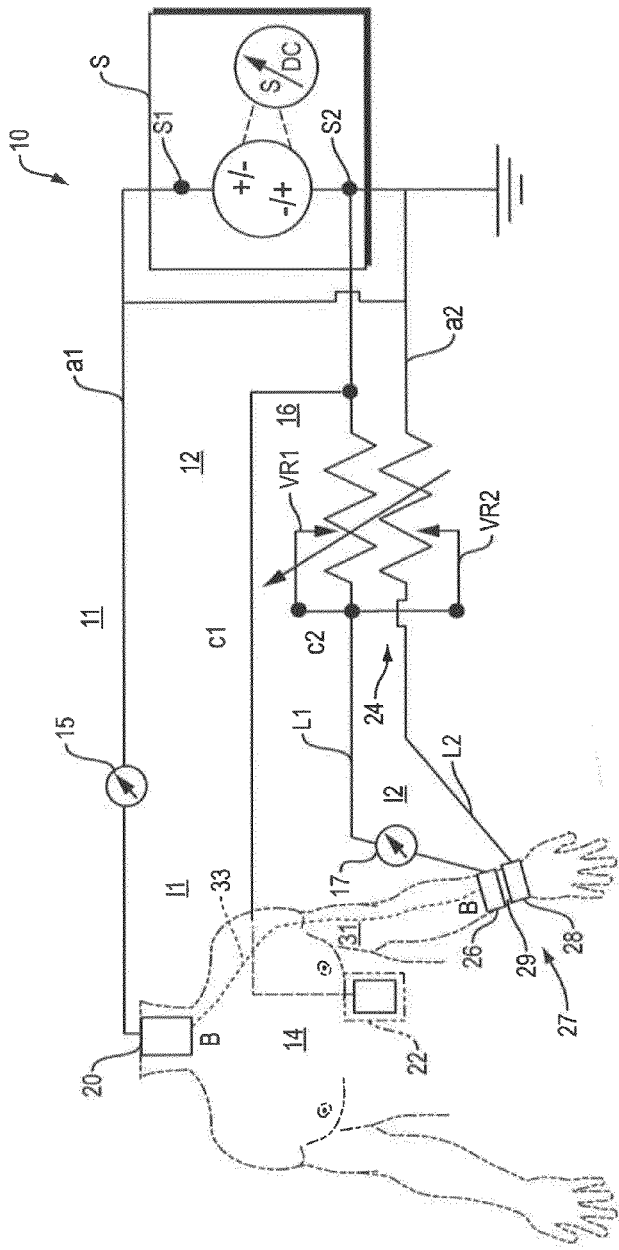
FIGS. 1 and 2: Illustrate an embodiment of these teachings for regulating the median nerve for resolving a chronic fisted hand and fingers with high muscle tone.

The description is not to be taken in a limiting sense, but is made merely for the purpose of illustrating the general principles of these teachings, since the scope of these teachings is best defined by the appended claims.

The above illustrative and further embodiments are described below in conjunction with the following drawings, where specifically numbered components are described and will be appreciated to be thus described in all figures of the disclosure:

As used herein, the singular forms "a," "an," and "the" include the plural reference unless the context clearly dictates otherwise.

Definitions

The following definitions pertain to the present disclosure, with the understanding that such may be modified by context of use. For purposes of the teaching of the present teachings:

The term "nerves" may be referred to herein as including nerves, neurons, motor neurons and interneurons and the like, and are generally referred to herein as "nerves" or "neurons";

The terms or concepts of nerve stimulation and neural stimulation are used liberally and interchangeably to describe applications of the stimulation of the teachings;

The terms neuromodulation, modulation, stimulation and regulation are used interchangeably as equivalents for purposes of this disclosure and indicate an effect imposed upon a target in practice of present teachings;

The terms dysfunction, disorder, defect and abnormality are used interchangeably as equivalents for purposes of this disclosure and indicate the concept of medically recognized conditions suitable for medical intervention:

The term effector organ refers to a neurally-ennervated organ that produces an effect in response to nerve stimulation. Muscles are included within such definition for purposes of this disclosure. The effects of stimulation of the present teachings upon an effector organ or muscle may be discussed interchangeably for purposes of inclusive discussion of the present teachings.

The term "stimulation," as used herein, refers to either excitation or inhibition of nerve fibers, also referred to as up regulation or down regulation.

The term "electrical stimulation," as used here in refers to the production or introduction of current into spinal nerve, neuron, circuit or pathway, whether by applying a voltage or magnetically inducing a current.

Improved method and apparatus for neuromodulation and regulation of effector organs are disclosed herein below.

In one or more embodiments, the system of these teachings includes a first stimulation component configured to provide stimulation of a nerve associated with a target effector organ and a second stimulation component configured to provide spinal direct current stimulation associated with modulation of said target effector organ.

In one instance, an embodiment of the system of these teachings also includes a controller component configured to simultaneously control the range of current supplied by the first and second stimulation components.

In one instance, the first stimulation component includes a first electrical source with positive and negative terminals providing stimulation current to stimulation electrodes, including two electrodes disposed for stimulation of a nerve associated with a target effector organ; one electrode operatively connected to the positive terminal and another electrode operatively connected to the negative terminal; each one of the two electrodes being electrically insulated from the other one of the two electrodes. In one embodiment, the two electrodes are located noninvasively and are skin-surface electrodes. In another embodiment the two electrodes are implanted electrodes. In one instance, the first electrical sources also implanted and the controller component is operatively connected to the first electrical source by a wireless connection.

In one instance, the second stimulation component includes a second electrical source having a second positive terminal and a second negative terminal, a first electrode disposed to be placed at a. spinal cord location and a second electrode disposed to be placed at a location selected from another location at the spinal column or a location distal from the spine. One of the first and second electrodes is operatively connected to the second positive terminal and another one of the first and second electrodes is operatively connected to the second negative terminal.

In one embodiment, the first and second electrical sources are the same source. In another embodiment, the first and second electrical sources and the control component are located in a wearable housing. In one embodiment, the source is a DC source. It should be noted that embodiments in which the first electrical source is a pulsed source, such as a pulsed DC source, are also within the scope of these teachings. Although less frequently used, embodiments in which the source is a pulsed AC source are also within the scope of these teachings.

Many abnormalities and dysfunctions are associated with regulation of effector organs, which may be based on disturbances in the nervous system. Management of such abnormalities by regulation of effector organs, including regulation of muscle tone abnormalities, is a serious and sometimes insurmountable challenge. Embodiments of the present teachings are directed to meeting the need for stimulation systems utilizing improved neuromodulation for control of abnormalities associated with effector organs in vertebrate beings.

Embodiments of the present teachings feature applications of direct current stimulation (DCS) at the spinal cord and in various embodiment includes stimulation of an associated nerve. Such associated nerve may include a nerve associated with a particular effector organ for modulating control thereof or may be a peripheral nerve associated with a muscle for modulating control thereof.

Trans-spinal direct current stimulation (tsDCS) modulates spinal nerves, neurons, circuits and pathways. Embodiments of the present teachings, include tsDCS paired with a second neural stimulation set apart from the location of tsDCS spinal stimulation, and in that sense separated from or peripheral or distal to the location of spinal stimulation, and is therefore referred to herein as non-spinal or peripheral DCS (pDCS) for affecting an associated body part. This second stimulation includes applied-energy stimulation of a nerve associated with a target body part, such as a nerve to an effector organ, a peripheral nerve to a target muscle, or other nerve of interest, for achieving a particular outcome associated with the target body part. A target body part may include any part of the body having an associated nerve whose stimulation can modulate an associated function. As such, reference herein to the PNS and peripheral nerves will be understood as a reference to a subset of the systems and nerves associated with application of pDCS stimulation according to the present teachings. Thus nerves outside of the PNS and peripheral or distal to the spinal cord are within the term pDCS.

In an embodiment of these present teachings, spinal stimulation is delivered as non-varying (e.g., non-time varying) constant-current tsDCS. In embodiments of these present teachings, the tsDCS and a pDCS stimulation are delivered as non-varying constant direct current stimulations.

In embodiments of the present teachings, systems are configured for up-regulation and/or down-regulation of target effector organs for improved activity. In an illustrative embodiment, the present teaching is configured to provide down-regulation of muscle tone to reduce spasticity or up-regulation of muscle tone to reduce flaccidity. Embodiments of the present teachings for treating hypertonia and reducing muscle tone feature anodal tsDCS and cathodal pDCS, as generated by cooperation of the anode of a spinal direct current stimulation circuit and the cathode of a peripheral nerve direct current stimulation circuit of the present teachings ("spine-to-nerve"). Embodiments of the present teachings for treating hypotonia and increasing muscle tone feature anodal pDCS and cathodal tsDCS, as generated by cooperation of the anode of a peripheral nerve direct current stimulation circuit and the cathode of a spinal direct current stimulation circuit of present teachings ("nerve-to-spine).

In practices of the present teachings, we teach application of positive and negative signals to define direct current electrical circuits for stimulation of a nerve associated with an effector organ having an abnormality associated therewith and for stimulation of a location on the spinal cord, such as at nerves of a spinal enlargement location, which is neurally associated with that nerve and organ, thus defining a neural pathway of interest.

In practices of the present teachings, if a particular body part has a neurological abnormality, then an associated nerve may be stimulated to regulate activity of such body part. In one embodiment, a spinal stimulation circuit is established by placing a spinal stimulation electrode at a spinal location adjacent to a selected spinal nerve communicating via a connecting neural pathway with a nerve associated with regulation of said body part, and the spinal stimulation circuit having a reference electrode placed anterior to the spine.

In one such embodiment, a neural stimulation circuit is also established at a peripheral (i.e., non-spinal) nerve associated with regulation of that body part, such nerve normally communicating via the connecting neural pathway to that selected spinal nerve. A pair of electrodes are located across a section of such peripheral nerve, a first electrode being proximal to the spine and a second electrode being relatively distal to the spine relative to that neural pathway. In various embodiments, this array of electrodes is provided as a charge-balancing electrode device including a first electrode and second electrode arrayed as insulated electrodes on a flexible substrate and having exposed electrode surfaces and configured to be placed or affixed across a section of the target nerve associated with the effector organ of interest for polarization of the nerve section. Thus the first and second electrodes are either anode or cathode and cooperate as opposite poles of the neural stimulation circuit to deliver the pDCS non-spinal, peripheral direct current stimulation of the present teachings.

The spinal stimulation electrode and the spinal reference electrode are either anode or cathode and cooperate as opposite poles of the spinal stimulation circuit. Interaction of a pair of proximal poles between these two circuits, spinal and peripheral, as anode and cathode, establish a third resulting polarization circuit of these teachings to modulate the level of excitability of spinal motoneurons and interneurons as will address the neurological abnormality of interest, such as, for example, for regulation of muscle tone.

These stimulation circuits have directional current flow between positive and negative poles, i.e., between defining electrodes. It is the interaction between respective poles of these stimulation circuits that produces the desired polarizing current flow of the third circuit.

In practice of these teachings, a polarizing current flow of the resulting polarization circuit is defined between a respective anodes and cathodes of spinal stimulation circuits and neural stimulation circuit, for polarizing neurons, motoneurons and interneurons, along the connecting neural pathway between such spinal location and target nerve, e.g. a peripheral nerve. In embodiments of the present teachings, the resulting polarization circuit is defined by: (1) direct current flowing from spinal cord to nerve, spine-to-nerve, anode-to-cathode inhibits spinal motor neurons and interneurons, hence down-regulating the nerve of interest and reducing muscle tone at the muscle of interest; or (2) direct current flowing in the opposite direction from nerve to spinal cord, nerve-to-spine, cathode-to-anode, excites spinal motor neurons and interneurons, hence up-regulating the nerve of interest and increasing muscle tone at the muscle of interest. Current intensity is constrained to be equal to or greater at the spinal stimulation circuit versus at the neural stimulation circuit.

Practices of these teachings demonstrate marked effects of DCS on function of effector organs, including regulation of muscle tone. Muscle tone abnormalities impact treatment of many neurological conditions and severely limit recovery of motor control. Muscle tone depends on the level of excitability of spinal motoneurons and interneurons. In control mice and mice with spinal cord injuries with spasticity, spinal-to-sciatic DCS reduced transit and steady stretch-induced nerve and muscle responses. Sciatic-to-spinal DCS caused opposite effects. These findings provide the first direct evidence that trans-spinal DCS can alter muscle tone and demonstrate that this approach can reduce both hypotonia and hypertonia. We have found similar effects in humans.

We have shown that dorsal surface anodal stimulation of the spinal cord decreases spinal excitability, while cathodal stimulation increases excitability, and we have shown that trans-spinal direct current stimulation (tsDCS) modulates spinal neuron excitability, and that tsDCS modulates the excitability of primary afferent fibers via their presynaptic terminals. These findings of the presently disclosed teachings enable clinical trans-spinal DCS applications for treating effector organ and muscle disorders. In one practice of these teachings, disorders of maladaptive excitation-inhibition balance are treated, demonstrating substantial reduction in spasticity.

The present teachings have been demonstrated in mammals, including mice and humans. Significant to human therapeutic application, a six year old male child with chronic fisted hands, diagnosed with spastic cerebral palsy, was treated in practice of these teachings. After 10 minutes stimulation in practice of the teachings on the right hand, exceptionally high muscle tone and spasticity was reduced and the fisted hand unfolded. The result has been persistent. In a second session, after 10 minutes stimulation in practice of these teachings on the left hand, exceptionally high muscle tone and spasticity was reduced and the fisted hand also unfolded. The result also has been persistent.

Common muscle groups that can be treated in practice of these teachings, along with characterization of alternative treatments, are shown in attached Table 1. This is a sample of muscle groups and body parts that can be treated in practice of these teachings. Pharmacological treatment options, side-effects and surgical options are shown in Tables 2, 3 and 4.

Embodiments of the present teachings provide method and apparatus for control and modulation of effector organ activity, such as modulation of muscle tone through dual applications of direct current stimulation: trans-spinal direct current stimulation tsDCS at the spinal cord coupled with other direct current stimulation pDCS at a peripheral location and nerve associated with treatment of an abnormality. In practices of the presently disclosed teachings, dual simultaneous DCS affects effector organs by modulating spinal cord excitability, wherein these teachings modulates background activity level of the motoneuron pool to change the firing threshold of the motoneurons.

The present teachings meets the long felt need for improved method and apparatus for enabling restoration of effector organ functions and regulation of muscle tone. In one aspect of the teachings, a neuromodulation system includes two sources of constant DCS for simultaneous provision of stimulation applied independently to the spine and to nerve(s) associated with a target to be treated. We disclose method and apparatus for modulating of spinal cord excitability, including use of tsDCS modulation of spinal cord excitability coupled with pDCS (the latter preferably featuring a segment of polarized nerve achieved with a charge-balancing electrode device of these teachings). In an embodiment of these teachings, simultaneous trans-spinal tsDCS and peripheral pDCS are provided for up or down regulation of various effector organ functions of interest.

Embodiments

The present work demonstrates effects of trans-spinal sciatic-to-spinal or spinal-to-sciatic direct current stimulation on physiological and pathological abnormalities in treatment of effector organs such as in regulation of muscle tone. Overall, these results show that DCS affects muscle tone by modulating spinal cord excitability and that simultaneous stimulation with the presently disclosed tsDCS combined with pDCS resolves muscle tone dysfunction with long term effect. This has substantial clinical value in treatment of a wide range of effector organ disorders.

Embodiments of the present teachings utilize special circuits: The first circuit involves current flow between a skin surface electrode positioned above the spinal cord and a reference electrode, the latter at an abdominal skin or other non-neural area, for delivery of tsDCS. In practice of these teachings, this current path fosters inhibition with an anodal spinal electrode and cathodal abdominal electrode or excitation when these polarities are reversed and current flows in the reverse direction. Typically, and compared to the peripheral nerve current path, relatively higher current intensity is needed in the spinal-abdominal current path to have consistent effects on spinal motor neurons and interneurons. The need for higher current intensities at the spinal cord might be due to the larger conductive volume and relatively greater distance between the spinal cord and the electrode. This circuit can be used to deliver tsDCS without other stimulation. However, the second circuit supplies peripheral nerve direct current stimulation, pDCS, and in conjunction with tsDCS, long term effects in spinal neuromodulation is achieved.

In regard to treatment of muscle tone, we find and adapt results showing: (1) local changes in the excitability of the distal nerve segment (e.g., sciatic) are not a factor in the action of trans-spinal DCS, however, (2) excitability changes in the proximal nerve segment (e.g., sciatic) are a critical factor in modulating DCS-induced muscle tone changes. This is supported by the finding that application of current to only a nerve circuit (e.g., sciatic) or an abdominal circuit had no effect on muscle tone; simultaneous stimulation of both circuits is required to change muscle tone in practice of these teachings.

The present results are the first demonstration of trans-spinal DCS-induced alterations in muscle tone, and they have great clinical applications. Trans-spinal DCS can be applied non-invasively to humans to treat or manage various muscle tone abnormalities. Moreover, tsDCS can be applied through implantable electrodes to manage severe conditions (e.g., dysfunctional bladder; dysfunctional anal sphincter and many others) using a benchtop, wearable or implantable stimulation system of these teachings. In addition, since spinal-to-sciatic DCS can increase muscle tone, it has the potential to amplify muscle tone in conditions in which muscle tone is abnormally low (e.g., patients with cerebellar deficits, spinocerebellar lesions and in developmentally-delayed children, including those with Down's syndrome).

Further illustrative and preferred embodiments of these teachings showing tsDCS modulation of spinal cord excitability for muscle tone regulation, method and apparatus, for use in mammals, are provided below. Embodiments of these teachings enable treatment of mammals, especially humans, non-invasively or with use of an implant, to achieve the desired outcome of well-regulated effector organs and muscles. In applications, tsDCS+pDCS, spinal-to-nerve (positive to negative) or nerve-to-spinal (positive to negative), modulates spinal neuron excitability and activity, down or up, as indicated, respectively.

The present teachings teach applications of trans-spinal DCS to affect muscle tone by modulating spinal cord excitability and is applied in treatment of living beings, in both human and veterinary applications. Practices of the present teachings treat hypertonic or hypotonic conditions. In one illustrative practice of the present teachings, we treat a spastic band in patients having spastic cerebral palsy, by down-regulation of the high muscle tone. In another practice, we treat weak muscles such as at lower limbs in patients with Down's syndrome, by up-regulation of muscle tone. These are examples by way of illustration and not by way of limitation of the scope of these teachings.

Figure 2:
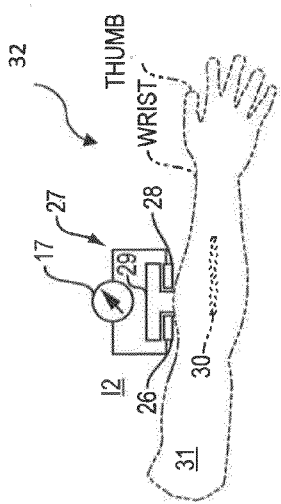

FIGS. 1-2 show an embodiment of the present teachings providing an effector organ regulating device 10 having a tsDCS–pDCS stimulation circuit 11 for modulating spinal cord excitability. Circuit 11 is driven by variable constant DC source S at inputs S1 and S2 (either internal to the system or from external power source). Depending upon desired direction of current flow, S1 and S2 are positive or negative. For a muscle tone down-regulating configuration of device 10, source S1 and the spinal electrode 20 are positive, and source S2 and the proximal distal nerve electrode 26 are negative. For an up-regulating configuration of the device, source S is switched accordingly to apply DC with S1 negative and S2 positive, and thus the spinal electrode would be cathodal and the proximal nerve electrode anodal. This switching can be accomplished internal or external to device 10, although it is preferred that all electrode sources are switched internally and simultaneously so as to avoid unwanted combinations of polarities being presented to the electrodes.

It will be appreciated that, in various embodiments of this disclosure, the modulation circuit is shown having nomenclature a1, c1, a2, c2, indicating specific anodal and cathodal branches as would apply to the down-regulating embodiment of anodal spinal and cathodal nerve. More specifically, in FIG. 1 this would be correct where input S1 is positive and S2 is negative, however this is a matter of illustration and not a matter of limitation of the disclosure and reversal of S1 and S2 will convert the same circuit to anodal nerve and cathodal spinal for muscle tone up-regulation. Safe operating condition is spinal current I1 equals or is greater than neural current I2.

Regulating device 10 will either down-regulate (inhibit) or up-regulate (excite) to modulate activity associated with a target effector organ. The present method and apparatus can be applied to down-regulate muscle tone to relieve a fisted spastic hand and fingers or can be similarly applied to other muscles of interest. Direction of current flow determines function. Modal spine to cathodal nerve stimulation will down-regulate muscle tone so as to reduce spasticity and rigidity, while modal nerve to cathodal spine stimulation will up-regulate muscle tone so as to reverse flaccidity.

FIGS. 1 and 2 illustrate an example of regulation of the median nerve for resolving a chronic fisted hand and fingers with high muscle tone. Stimulation circuit 11 has a spinal branch 12 for supplying sub-threshold stimulation to the spinal cord 14 at a first current level I1, measured at ammeter 15, and has a neural branch 16 for supplying to the nerve of interest (e.g., median nerve) sub-threshold stimulation at a second current level I2, measured at ammeter 17. When setting up for treatment, the current I2 is brought up to measurable EMG and then reduced to subthreshold (no apparent nerve activity). Meanwhile, spinal DC is always subthreshold because of its low intensity (about 2 to 4 mA) when applied on the surface of the skin. However, in the case of implantable spinal electrodes, these intensities might produce activity and in this case adjustment would be made to reduce currents until no apparent nerve activity is observed.

Spinal branch 12 includes spinal electrode 20 positioned at the spinal cord 14. In some embodiments, the location of electrode 20 on the spinal cord is at the cervical enlargement for upper limb muscles to be treated and at the lumbar enlargement for lower limb muscles to be treated, as will be appreciated by a person skilled in the art. For treatment of hand and fingers, it is at the cervical enlargement E–1 behind electrode 20 in FIG. 1. A reference electrode 22 (return electrode) is positioned on an anterior location, such as the abdomen, as shown, or a bony location or the like.

In practices of the present teachings, the nerve stimulation is charge-balanced, wherein the nerve is stimulated using an electrode array presented as charge-balancing electrode device 27 for the neural electrodes. This charge-balancing electrode array of device 27 has two insulated and oppositely charged electrodes 26, 28 which are mated in fixed relation on an insulating layer 29. This fixed device 27 is placed with the two opposite charged electrodes across the nerve segment 30, with minimized separation for the purpose of reducing the risk of damaging effects of monopolar stimulation along a greater length of the nerve as may have a long term polarizing effect.

Care is taken to achieve sub-threshold current density upon the stimulated nerve area. As well, as earlier described, the rationale for creating and placing our charge-balancing electrode device 27 upon the target nerve is to reduce the potential for damaging effects of monopolar stimulation at the nerve. The charge-balancing electrode device 27 as described above works at the neural location to assure safe application of neural stimulation, maintaining fixed and close relation between fixed electrodes 26, 28. This shortened length of nerve that is enervated bounded by the fixed cathodal and anodal electrodes will obviate and minimize risk of any such damaging effects.

Neural branch 16 includes a charge-balancing circuit 24 comprising variable resistor VR1 defining a first leg L1 resistively connected between input S2 and proximal electrode 26 of charge-balancing electrode device 27, and also a variable resistor VR2 defining a second leg L2 resistively connected between input S1 and distal electrode 28 of the electrode device 27. Electrodes 26, 28 of charge-balancing electrode device 27 are mounted in fixed relationship on over local nerve segment 30'(FIG. 3) of nerve 30, in this example median nerve 30 on arm 31 shown in FIG. 2.

It will now be appreciated that in embodiments of the present teachings, a first pair of electrodes 20, 22 are part of a first stimulation circuit 12 to apply trans-spinal direct current stimulation (tsDCS) to the spine 14 and a second pair of electrodes 26, 28 are part of a second stimulation circuit 16, the latter to apply stimulation to nerve 30 associated with the target body part. In turn, these two circuits define a resulting polarization circuit 33 defined between respective electrodes 20 and 26, shown in FIG. 1 as between an anodal electrode 20 of the spinal circuit 12 and a cathodal electrode 26 of the neural circuit 16. The resulting polarization circuit 33 stimulates the spine and achieves a desired regulation of excitability of effected spinal motoneurons and interneurons that enables the desired outcome of regulation of muscle tone.

Figure 10B:
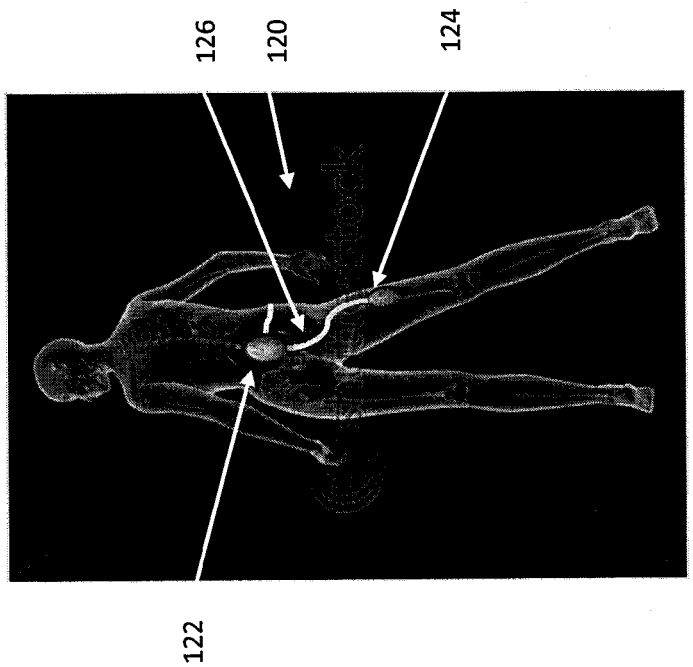
FIGS. 10A-B: Show a wearable tsDCS device of these teachings.
Figure 10A:
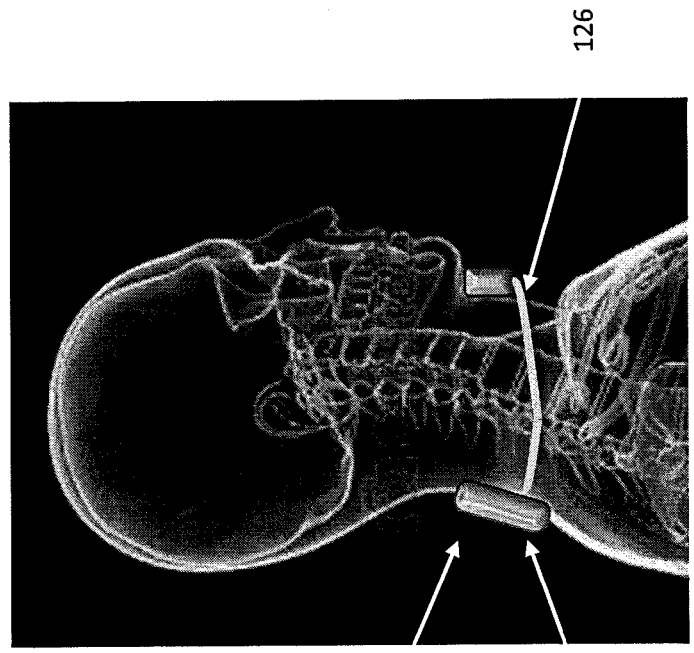

The active spinal electrode 20 is preferably located at a spinal enlargement 1, 2 FIG. 10. The spinal enlargement is selected as being associated with a nerve that is associated with control of the body part of interest, A reference spinal electrode (second pole) is affixed at an anterior location such as at the abdomen. The tsDCS is applied between these two electrodes/poles to electrically polarize the zone of tissue between the two electrodes. In this embodiment, the second polar circuit 16 is located at and energizes peripheral nerve 30 associated with control of the target body part (arm/hand). The proximal and distal electrodes 26, 28 (i.e., two poles) of this circuit 16 are arrayed over the target nerve 30 to define a short stimulation section 30' of that nerve between these two electrodes (poles) this limits the reach of polarization at this nerve 30.

Such second stimulation circuit can be applied to locations in many parts of the body and the character of stimulation energy will be selected accordingly. In the embodiment of FIGS. 1-2, peripheral nerve direct current stimulation (pDCS) is applied between electrodes 26, 28 to create a zone of polarization across nerve section 30'.

Figure 3:
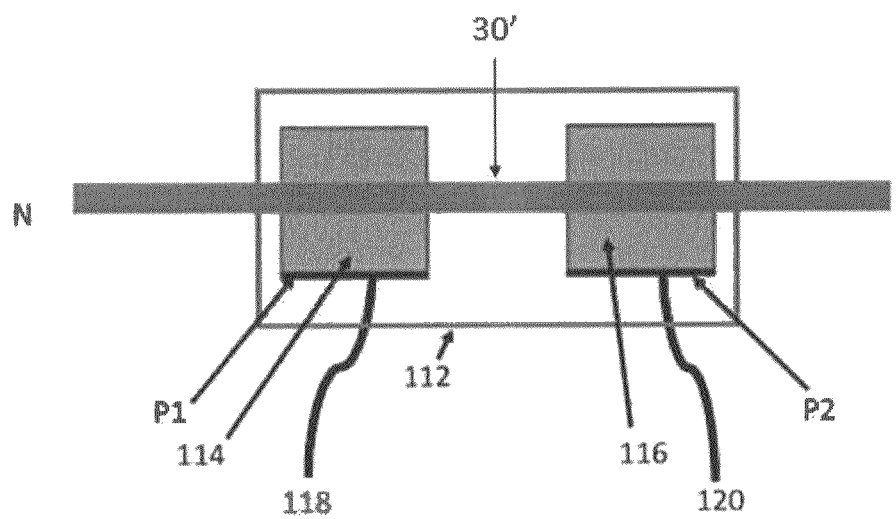
FIG. 3: Charge-balancing electrode device.

Down regulation and up regulation of muscle tone are guided by the direction of the interaction between these adjacent electrodes of the spinal and neural circuits 12, 16 that define the polarization circuit 33. For down-regulation, the spinal electrode 20 is positive ("anodal") and proximal peripheral nerve electrode 26 must be negative ("cathodal"). This defines the needed spine-to-nerve polarization circuit 33 (polarizing current flow path) between these two energized electrodes of the two polar circuits 12, 16 for down-regulation. For up-regulation, the proximal nerve electrode 26 is positive ("anodal") and spinal electrode must be negative ("cathodal"), This defines the needed nerve-to-spine polarization circuit 33 (polarizing current flow path) between these two energized electrodes of the two polar circuits for up-regulation, FIG. 3 shows another embodiment of charge-balancing electrode device 27 having electrode conductive pads 114, 116 mounted on non-conductive substrate 112, and as applied in contact with nerve N. Electrodes 114, 116 are attached to substrate 112 in inset metal pockets P1, P2 which are in contact with electrical leads 118, 120 (or alternatively electrodes 114, 116 are attached in direct contact with ends of the leads without using the metal pockets P1, P2). The electrodes are preferably sponge electrodes with conductive gel. In one embodiment, the substrate 112 is 8 cm×6 cm and the sponge pads 114, 116 are 2.5 cm square affixed in the metal pockets P1, P2 on insulating substrate 112, wherein the sponge pads are separated by 2 cm as affixed.

Returning to FIGS. 1-2, neural proximal and distal electrodes 26, 28 always have opposed polarities from each other, and the polarity of spinal electrode 20 is always opposite polarity to its own reference electrode 22 and to the polarity of the proximal neural electrode 26. Reversal of polarity of the adjustable Source S and thus at S1/S2 reverses the polarity of the entire circuit 11, thus maintaining this oppositional relationship. When the spinal electrode 20 is positive (and its reference electrode 22 is negative), the neural proximal electrode 26 is negative and the distal electrode 28 is positive; and vice versa when polarities of S1 ,S2 are reversed.

As shown in FIG. 1, the present teachings provides a regulating device 10 having tsDCS–pDCS stimulator 11 circuits that form the desired resulting polarization circuit 33 and that can be used either for down-regulating or up-regulating effector organ activity including muscle tone. In one practice of these teachings, an isolated power supply having two separate 18 volt battery sets supply isolated constant current to the two circuits 12, 16 from the adjustable DC source S, at S1 and S2.

Referring to FIG. 1, when S1 is positive and S2 is negative, in a down-regulation embodiment, the circuit inhabits spinal motoneurons and interneurons and reduces muscle tone at the muscles associated with the stimulated nerve. When the signals at S1 and S2 are reversed, i.e., where S2 is anode and S1 cathode, the device operates to excite spinal motoneurons and interneurons and increases activity at the effector organs, e.g., muscle(s) of interest associated with the chosen nerve being stimulated.

In some experiments, current in circuit 11 was applied in the relation of spinal current I1 to distal neural current I2 sometimes at around 160:1 in mice and around 2:1 to 3:1 in humans. But in all subjects the ratio can range depending upon body size, type, age, fat level, etc., as well as the specific neurological deficit, or whether the nerve of interest is less responsive or not easily stimulated from the surface, and this will impact needed levels of current stimulation. Even so, the present teaching is easily setup and operated in veterinary and human practices even where these ratios may vary widely patient to patient.

The electrodes of regulation device 10 are attached to the subject and the spinal circuit is properly set. An electromyography (EMG) device 32 is connected to monitor increased stimulation at the muscle of interest associated with the nerve as stimulated by the current flow. As will be appreciated by a person skilled in the art, in the present example of the median nerve stimulation, the EMG was attached across the thumb to measure action potential at the abductor pollicis brevis muscle (on the palm side of the hand). The pre-treatment clenched fist and EMG attachment at the thumb is indicated in FIG. 1 and FIG. 2. Post-treatment, spasticity was reduced as the hand and thumb were now relaxed and extendable, and no longer clenched.

In an illustrative embodiment, the following method was followed for treatment of spastic hand in a seated patient. The method featured anodal spinal electrode and cathodal proximal electrode at median nerve to decrease muscle tone of a rigid hand and fingers. This is shown by way of illustration and not as limitation of the spirit and scope of the present teachings.

Spinal electrode placement: the anode electrode placed over the cervical region to cover C6 to the upper edge of T1. (Before placing each electrode, the skin should be thoroughly cleansed with alcohol.)

Abdominal electrode: cathode electrode placed over anterior abdominal skin or other location that is not a major neural location.

Median nerve electrode placement: a charge-balancing electrode device with two separate electrodes: the distal electrode (toward the hand) as anode; the proximal electrode (toward the head/cervical enlargement) as cathode. Preferably the double electrode set is placed over the front aspect of the wrist joint across and over a section of the median nerve.

Electromyography electrode placement: bipolar electrodes record EMG from thumb muscles, placed over the abductor pollicis brevis (APB).

Tuning the stimulator: The stimulator output is brought to threshold and reduced to produce no EMG activity from the nerve/muscle. In illustrative practice of these teachings, about 4 mA at the spinal-abdominal circuit and about 2-3.5 mA at the median nerve circuit achieves desired results in a human. However, in small subjects the branch values may converge, such as 2-2.5 mA at both the nerve and spinal column. In the case of such a subject, typically a child, the adjustable power source S would be adjusted to bring the spinal circuit to about 2-2.5 mA and the variable resistor VR1-VR2 would be adjusted, thus bringing the nerve electrode set also to about 2-2.5 mA. In this case the current ratio I1:I2 would be as close as 1:1.

Typical treatment duration: The duration is for 20 min. (At beginning/end of treatment ramping up/down is recommended for comfort.)

End of treatment: Turn the stimulator off (after ramping down to zero input). Inspect the skin under the electrodes for any skin changes.

In illustrative practices of these teachings, current at the spinal cord is first adjusted typically 2-4 mA on average, depending on age and body type/size, and access to nerve, etc., as would be appreciated by a person skilled in the art. Generally, larger and stronger patients require higher current level, and the spinal cord accepts a much higher dose versus the current at the more sensitive target nerve. However, if the nerve is buried or accessed through much tissue—possibly scarred or fatty—a higher stimulation level of the nerve may be required. In some examples, there is low or no divergence of the spinal and nerve values, such as, for example, for an infant 2.5 mA at both spine and at nerve can be used. This low end regimen shows caution for the pediatric application and yet still achieves excellent modulatory results. Spinal current may be reduced to reduce artifact at spinal electrode. Preferably electrodes are sponge-type and are applied with conductive gel.

Placement of Electrodes:

In embodiments of these teachings, for treating upper limb conditions, peripheral stimulation is at the level of the median nerve, ulnar nerve, radial nerve, brachial plexus, or smaller branches thereof, and for treating lower limb conditions, peripheral stimulation is at the level of the femoral nerve, sciatic nerve, peroneal nerve or smaller branches thereof. As such, tsDCS devices are applicable to the treatment of disorders and dysfunctions of effector organs, including treatment of muscle tone impairments in patients with cerebral palsy, Parkinson's disease, stroke, traumatic brain injury, spinal cord injury, restless leg syndrome, spastic paraplegia, cerebellar lesions, developmental disorders such as Down's syndrome, specific genetic diseases with muscle tone impairment, and many other disorders affecting control of skeletal muscle.

Application of the present trans-spinal direct current stimulation in humans applies to treatment of many abnormalities. Anodal spinal to cathodal proximal nerve treatment is used for high muscle tone treatment, for example: spasticity and rigidity from various sources, including after stroke; spasticity after spinal cord injury; spasticity and rigidity in cerebral palsy; rigidity in Parkinson's patients; spasticity after traumatic brain injury; dystonia. Anodal nerve to cathodal spinal treatment is used for low muscle tone and flaccidity, such as due to genetic disorders (e.g. Down's syndrome) or due to disease, or cerebellar and other traumas including those caused by surgical interventions; among other cases.

Figure 4:
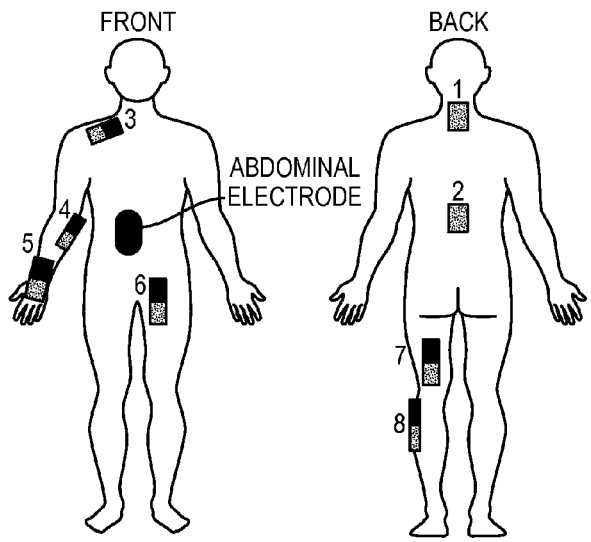
FIG. 4: Shows major nerve associations/combinations for electrode placement in human subjects, in illustrative practices of these teachings.

Electrode placement depends upon location of the muscles of interest and then upon identifying the associated nerve to be stimulated. Major nerve associations (i.e., cervical enlargement 1, lumbar enlargement 2, brachial plexus 3, ulnar nerve 4, median nerve 5, femoral nerve 6, sciatic nerve 7 and peronial nerve 8) are shown in FIG. 4 for preferred electrode placement in human subjects for down-regulating muscle tone. For down regulation, cervical or lumbar spinal electrodes are biased positive and the electrodes of the charge-balancing electrode device at the nerve of interest are presented negative (proximal)/positive (distal).

Practice of these teachings includes selectively applying peripheral stimulation to the muscles listed below associated with spinal stimulation to provide the indicated result with reduced muscle tone and reduced spasticity in the following combinations:

a) spinal stimulation at cervical enlargement with peripheral stimulation at: brachial plexus to reduce muscle tone of the whole arm; ulnar nerve to reduce muscle tone of the arm muscles associated with ulnar; median nerve to reduce muscle tone of hand and fingers; and b) spinal stimulation at lumbar enlargement with peripheral stimulation at: femoral nerve to reduce muscle tone of knee extensors; sciatic nerve to reduce muscle tone of knee flexors and all muscle of the leg and foot; and peroneal nerve to reduce muscle tone in the foot.

In another practice of these teachings, peripheral stimulation is applied to the listed nerves associated with spinal stimulation with the indicated result of reduced muscle tone and reduced spasticity in the following combinations:

a) anodal spinal polar stimulation at cervical spinal enlargement with cathodal peripheral nerve polar stimulation as treatment for indicated high muscle tone and/or spasticity, at: brachial plexus to reduce muscle tone of the whole arm; ulnar nerve to reduce muscle tone of the arm muscles associated with ulnar; median nerve to reduce muscle tone of hand and fingers; and b) anodal spinal polar stimulation at lumbar spinal enlargement with cathodal peripheral nerve polar stimulation as treatment for indicated high muscle tone and/or spasticity; at femoral nerve to reduce muscle tone of knee extensors; sciatic nerve to reduce muscle tone of knee flexors and all muscle of the leg and foot; and peroneal nerve to reduce muscle tone in the foot; and In another practice of these teachings, peripheral stimulation is applied to the listed nerves associated with spinal stimulation with the indicated result of increased muscle tone and reduced flaccidity in the following combinations:

cathodal spinal polar stimulation with anodal peripheral nerve polar stimulation as treatment for indicated low muscle tone, such as due to genetic disorders including Down's Syndrome, or due to disease, or cerebellar and other traumas including those caused by surgical interventions.

Figure 5:
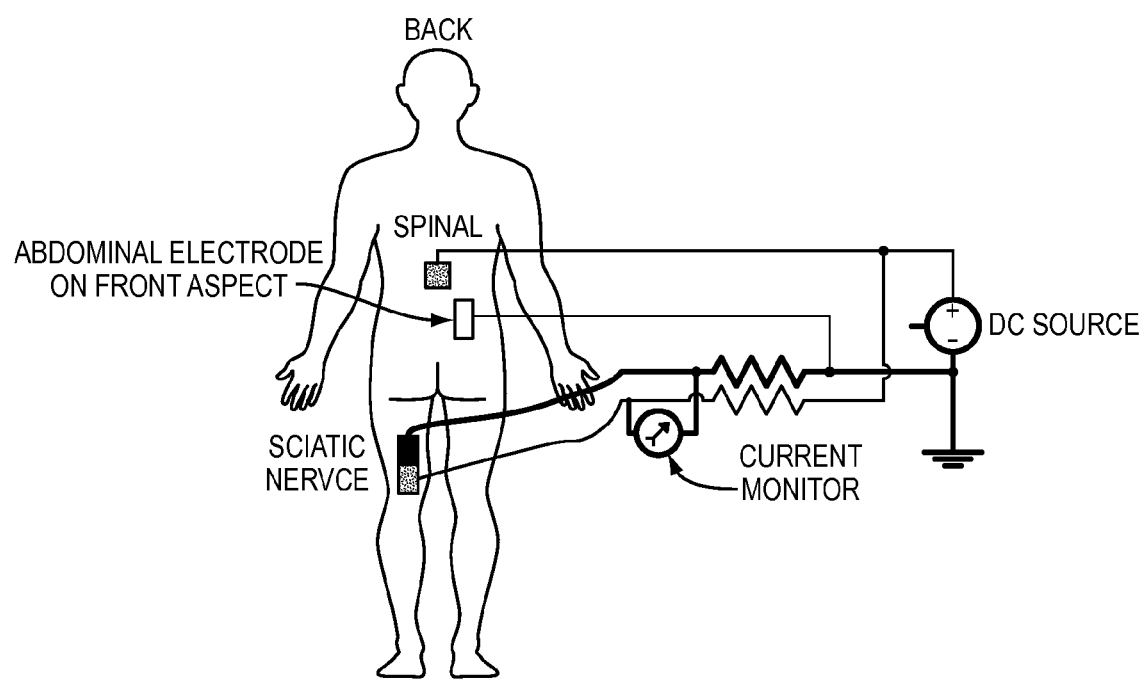
FIG. 5: Shows spinal-to-sciatic or sciatic-to-spinal treatment for muscles innervated by the sciatic nerve for either down or up-regulating muscle tone in the leg, depending upon signal polarity applied from the source. The configuration shown in FIG. 11 with anodal spinal cathode is for down-regulation.

In FIG. 1, the spinal branch 12 biases spinal electrodes 20, 22 and the nerve branch 16 biases the nerve set of electrodes of charge-balancing electrode array of device 27 in their complementary arrangements to achieve the desired current flow from anodal spine to cathodal nerve (muscle tone reducing) or from anodal nerve to cathodal spine (muscle tone increasing). FIG. 5 shows spinal-to-sciatic or sciatic-to-spinal treatment for muscles innervated by the sciatic nerve for either down or up-regulating muscle tone in the leg, depending upon signal polarity applied from the source. The configuration shown in FIG. 5 with anodal spinal electrode is for down-regulation.

Referring to embodiments of FIGS. 6-9, a packaged regulator system 50 includes a stimulator system and may be wearable, implantable, or stationary. Referring to FIGS. 6-9, in an exemplary system 50 incorporating the stimulation system 10 and muscle tone stimulator circuit 11 as earlier described, has an external spinal circuit 12* formed by coupling spinal electrodes 20, 22 via wires 72, 76 to male jack 70 having pins 74, 77 connecting to pins 56, 58 at mating female receptacle 54 on the system 50 housing, and which then is connected to the earlier described spinal branch 12.

An external neural circuit 16* is established by coupling neural electrodes 26 and 28 of charge-balancing electrode device 27 via wires 84, 86 to male jack 82 having pins 87, 89 for mating with receiver pins 62, 64 at mating female receptacle 60 on the system 50 housing, and which then is connected to the earlier described neural branch 16.

In one embodiment, to assure correct signals are delivered to the correct electrodes, spinal jack 70 preferably includes a detent feature 80 which must be accommodated by a cooperating detent feature 60 so as to enable mating of jack 70 and receptacle 54 in only one position to assure correct circuit connection. This arrangement assures that spinal electrode 20 will always be coupled via wire 72 and jack 70 to pin 56 of receptacle 54 and reference electrode 22 will always be coupled via wire 76 and jack 70 to pin 58 of receptacle 54. Furthermore, neural jack 82 preferably includes a detent feature 88 which must be accommodated by a cooperating detent feature 68 so as to enable specific mating of jack 82 and receptacle 60 in only one orientation to assure correct circuit connection for the charge-balancing electrode device 27. This arrangement assures that to assure correct signals are delivered to the correct electrodes and lessens the opportunity for human error in operation of the system.

In one practice of these teachings, of FIG. 1, electrode 20 is a sponge electrode and is color-coded such as with a blue marking ("B") and correspondingly electrode 26 of charge-balancing electrode device 27 is of opposite polarity and is color-coded with a marking ("B"). Reference electrode 22 and distal electrode 28 are black. The spinal electrodes 20, 22 are attached via jack 70 to system 50 and polarities are set for down-regulation or up-regulation, respectively, by user interaction with controller 90 and touch display 92. Controller 90 then assures that charge-balancing electrode device 27, attached via jack 82 to system 50, presents the blue-coded electrode 26 at opposite polarity to the other polarity of the blue-coded spinal electrode 20. This then assures that the resulting polarization circuit 33 is properly formed.

The user applies the spinal electrode 20 to the spine as earlier described. The user notes the blue-tagging and is reminded that the charge-balancing electrode device 27 must be placed over the nerve of interest with the blue-coded electrode 26 oriented proximal to the spinal electrode 20 and electrode 28 oriented distal to the spinal electrode 20. This prevents mistaken affixation of the charge-balancing electrode device 27, and prevents the wrong electrode 28 being placed where the correct electrode 26 should be placed. This error would present the wrong polarity electrode to resulting polarization circuit 33 and would make it ineffective.

Accordingly, the trained administrator always affixes the blue-coded spinal electrode 20 at the spine at the desired location and black-coded reference electrode 22 on a non-nerve location, as earlier discussed, and affixes the charge-balancing electrode device 27, preferably at an angle, e.g., at 90 degrees, across the nerve of interest (e.g., nerve 30, FIG. 1), to define a short length of nerve segment 30' to be stimulated, such that the oppositely-biased blue-coded electrode 26 of charge balancing electrode device 27 will be proximal to the blue-coded spinal electrode 20 and the black-coded reference electrode 28 of charge-balancing electrode device 27 will be distal to spinal electrode 20, all with appropriate polarities fixed. Signal levels are again adjusted as earlier discussed.

Thus the trained administrator enters data at input 92 and controller 90 of circuit 10 in system 50 which fixes spinal and neural electrode polarities and signal levels according to body type and whether treatment is for down or up-regulation of muscle tone. Blue spinal electrode 20 is positive for down-regulation (or negative for up-regulation) and is paired with proximal blue-coded electrode 26 which is oppositely negative (or positive) biased, while black reference electrode 22 is negative (or positive) and distal black electrode 28 is positive (or negative), respectively.

Figure 6:
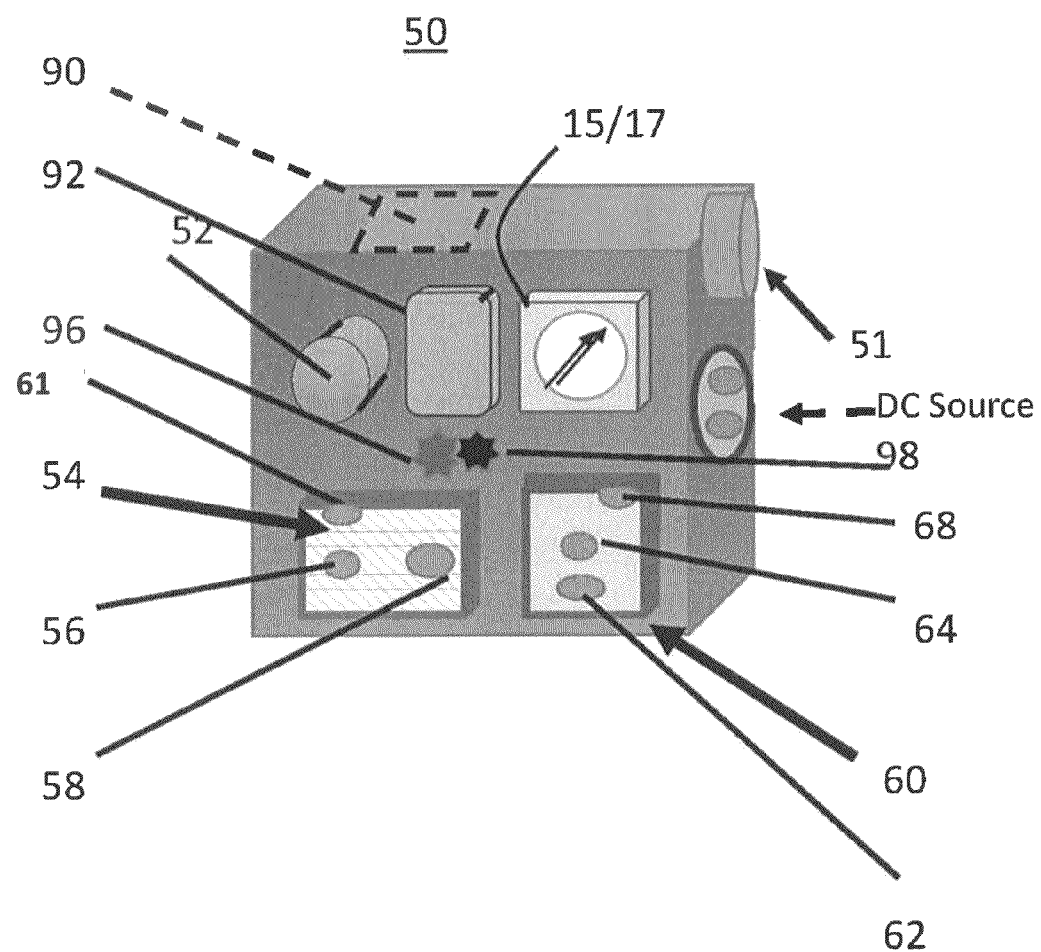
FIG. 6: Shows a packaged muscle tone regulator system in a practice of these teachings.
Figure 7:
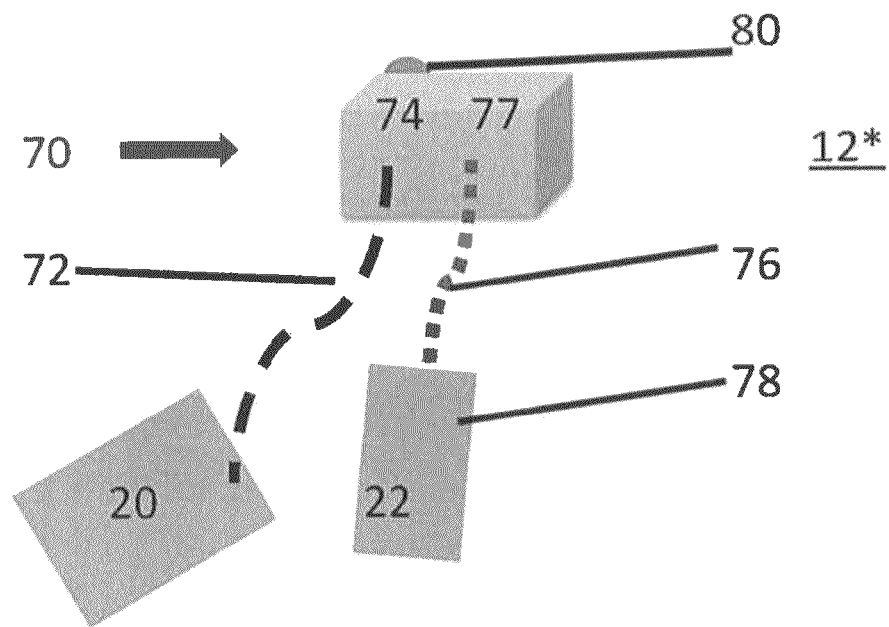
FIGS. 7-8: Shows special electrodes fixed neural electrode sets with leads in practice of embodiments of these teachings.
Figure 8:
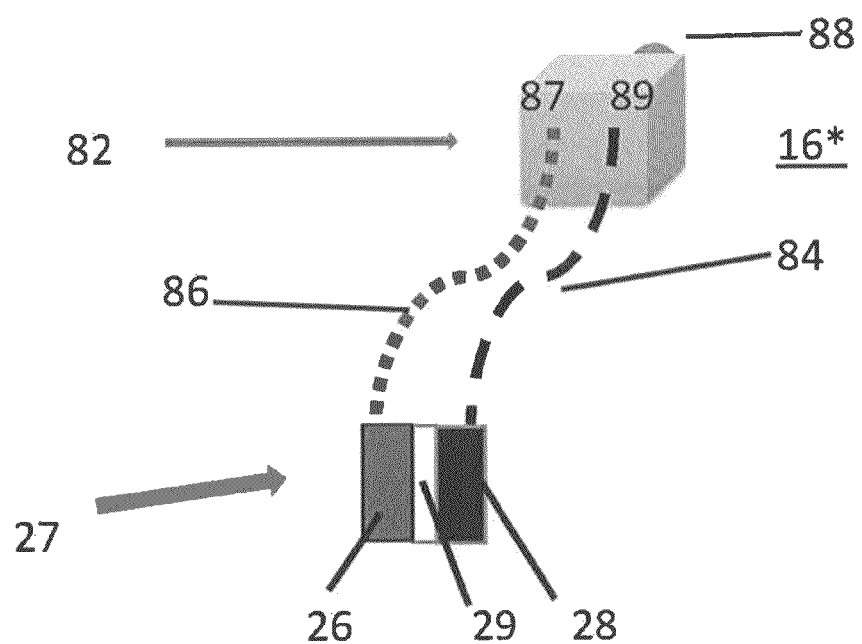
Figure 9:
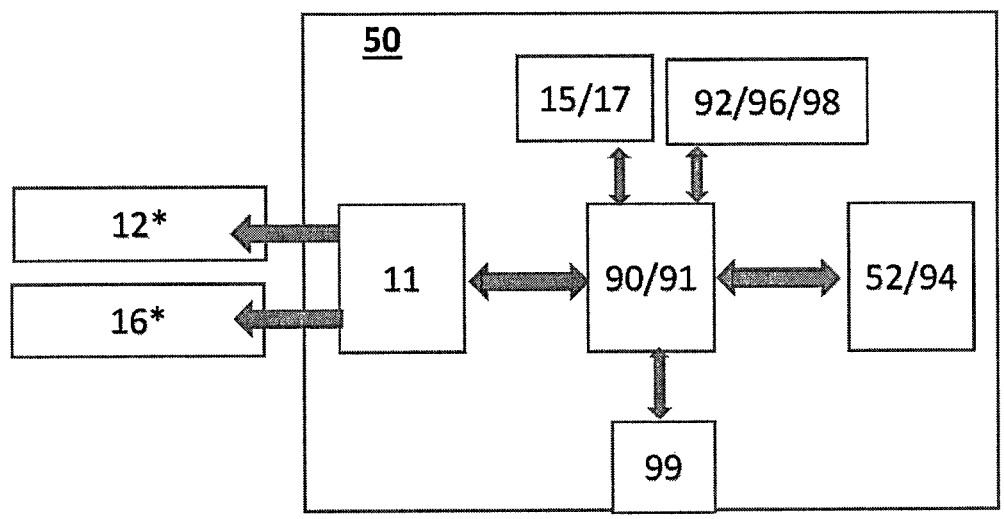
FIG. 9: Block diagram of an illustrative embodiment of these teachings.

In a further embodiment, a regulation system 100 of these teachings shown in FIG. 9 includes the above electrodes and jacks, formed as spinal connection device 12* and neural connection device 16*, for mating with receptacles 54, 60, of the included system 50, respectively. The system 100 includes DC power as part of or as supplied at DC source 94 which is controlled by controller circuit 90 for supplying and driving circuit 11 and for biasing electrodes 20, 22, 26, 28 via connection devices 12* and 16*. (FIG. 6 shows an external power source but either internal or external power source can be used for portable or workstation installation within practice of these teachings. Rechargeable batteries would be adequate.) User control interface is provided at touch screen and display 92. Power is adjusted at variable resistor 51 and VR1-VR2 resistive set 52 according to indications at ammeters 15/17.

It will be appreciated that the present teachings teach benchtop, wearable and implantable stimulation systems utilizing trans-spinal direct current stimulation for control of effector organs. Embodiments of these teachings enable regulation of effector organs and in one embodiment control of muscle tone. This may be achieved with a medical device with two sets of electrodes that are attached to the patient to provide spinal stimulation and peripheral stimulation, and may be presented as a benchtop stimulation system. In embodiments of these teachings utilizing implantable electrodes, wearable or implantable stimulation devices may be employed. For certain applications, administration of tsDCS therapy for disorders at effector organs will be sufficient if done between 1-5 times a week for a number of sessions on an outpatient basis. Indeed, we have seen beneficial results after a single treatment in a child with cerebral palsy who had clenched fists that had never been able to open spontaneously until treatment with an embodiment of the present teachings enable resolution of his hypertonia.

Figure 13:
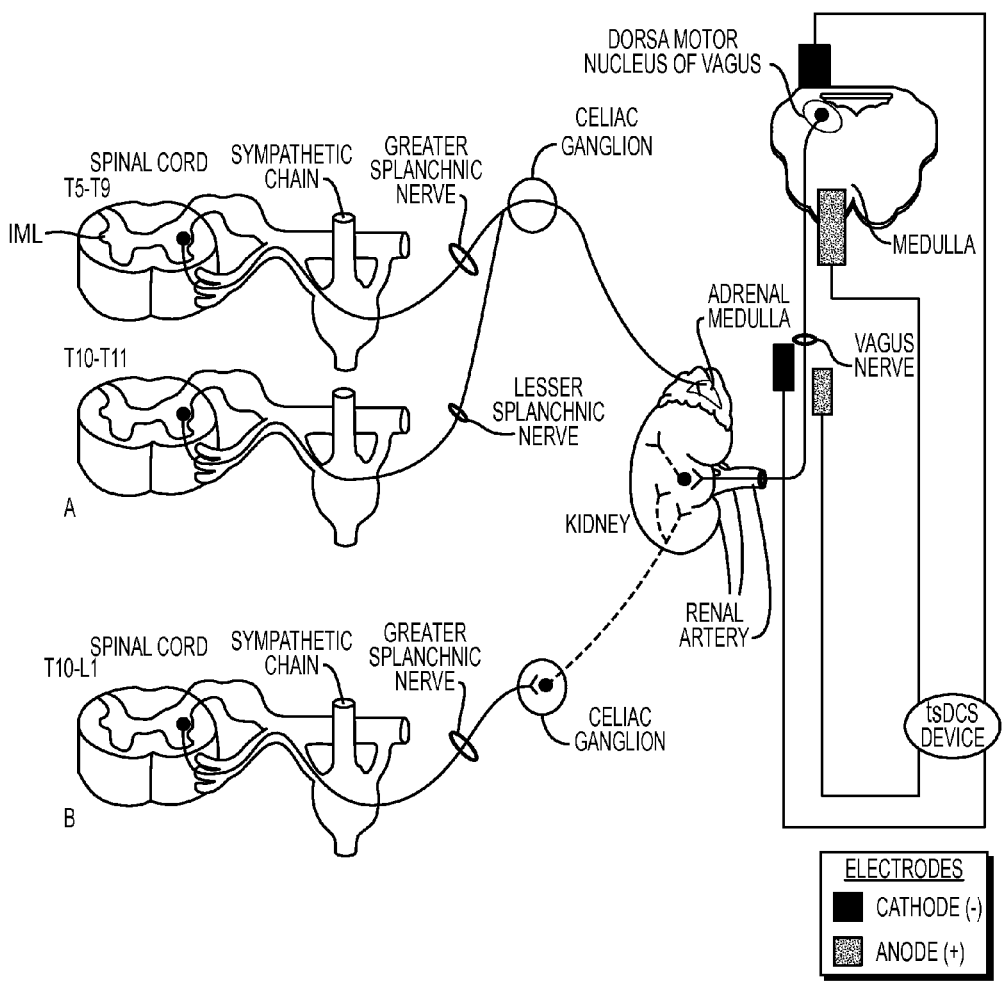
FIG. 13: Shows Neuromodulation strategy for modulating renal function based on increasing parasympathetic tone.

For some patients, treatment on such a schedule will be insufficient. Constant application of tsDCS, or application for several hours or sessions per day, for practical beneficial effects may be indicated for some. This can be assisted by enabling mobile delivery of such therapy. For such applications of tsDCS, embodiments of the present teachings are presented as a wearable on-skin device or implantable device as shown in FIGS. 4 and 13. Such devices are compact versions of these teachings. In one embodiment, the device footprint is shrunk to the approximate diameter of a silver dollar, and is attached to the skin surface of the spine with adhesive mounting, implanted magnets, or other methodologies. Pre-programming of microprocessor with memory 91 (FIG. 9) provides the capability to accommodate such long-term treatment, with adequate internal monitoring.

A tsDCS stimulation device delivers either anodal or cathodal direct current stimulation to the desired location on the spine, and in one practice with the tsDCS device here taught, device 120, FIG. 10, serves as the dorsal electrode 122 and the reference electrode 124 is placed on the skin surface of either the neck, abdomen, or other level depending on the spinal level of stimulation, neck attachment shown in FIG. 10. An electrode lead 126 runs along the skin from the wearable tsDCS device to the ventral skin-surface electrode 124. The wearable tsDCS device 120 comes in different sizes and form factors depending on whether it is being used with adults or children, and depending on the spinal location it is being used for. The wearable tsDCS device can be rechargeable, and removed at night for charging and comfort of sleep.

The wearable tsDCS device attaches to the skin surface of the spine at either the cervical, thoracic, lumbar or sacral levels depending on the effector organ to be stimulated. In certain embodiments, there is a pair of electrode leads for peripheral nerve stimulation coming off the wearable tsDCS device. Peripheral nerve stimulation can be done through skin-surface electrodes, subcutaneous electrodes, or implanted electrodes.

Figure 11:
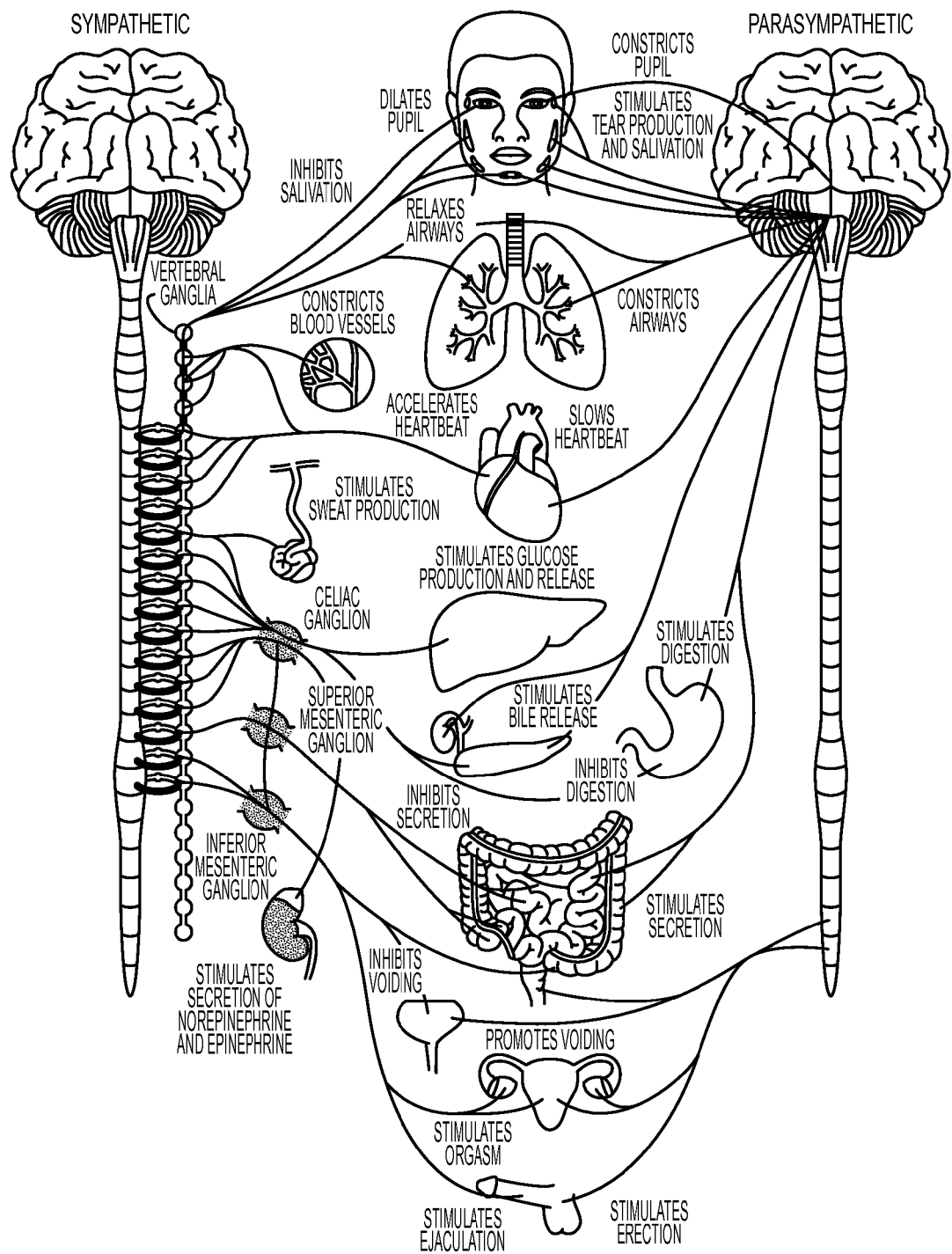
FIGS. 11 and 12: Show representations of the autonomic nervous system and sites of intervention.
Figure 12:
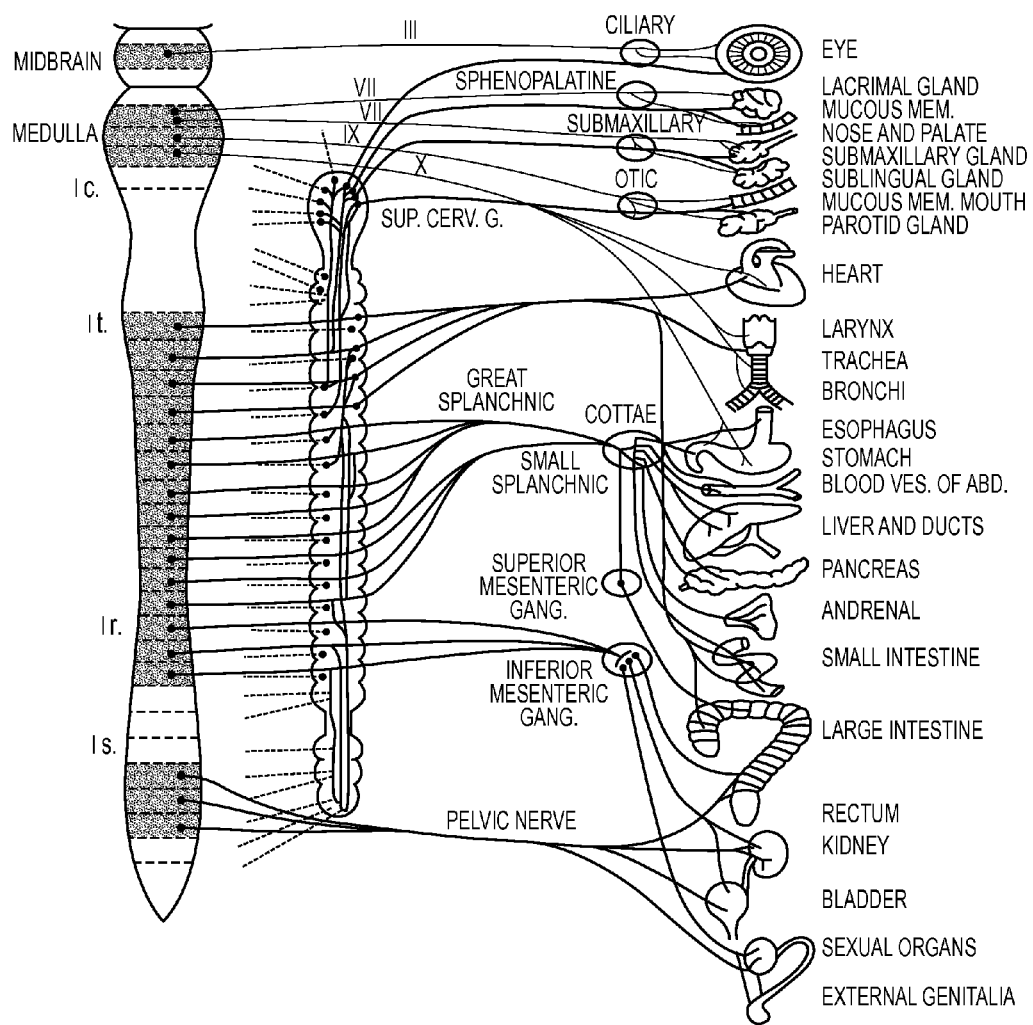

The autonomic nervous system controls and regulates numerous bodily functions including heart rate, respiration, digestion, urination, sexual response and others and consists of two major divisions, the sympathetic nervous system and the parasympathetic nervous system, shown in FIG. 11. Activation of the sympathetic nervous system results in preparation of the body for stressful or emergency situations, while activation of the parasympathetic nervous system results in conservation and restoration and controls body processes during normal situations.

The present teaching, including our wearable tsDCS device, by modulating spinal circuits at relevant spinal levels, can either activate or inhibit various parts of the sympathetic nervous system or the parasympathetic nervous system. There are myriad functions to be regulated in such a manner, and there are specific disorders related to dysfunction of either the sympathetic or parasympathetic system. Normal functions to be regulated by a tsDCS device of these teachings that modulate sympathetic or parasympathetic activity include modulating bronchodilation in the airways, modulating vasoconstriction in the skin and organs, stimulating gluconeogenesis and glucose release from the liver, stimulating secretion of epinephrine and norepinephrine by the adrenal gland, modulation of sweating, slowing or increasing heart rate, modulating tidal volume and rate of respiration, slowing or increasing intestinal processes involved with digestion, modulating urine production, modulating bladder contraction, modulating sphincter control, stimulating erection and sexual arousal, and others. Table 5 shows spinal levels of sympathetic outflow for various organs.

Beyond modulating normal functions, there are numerous disorders of the ANS that have been described and are referred to as dysautonomias, and can be due to failure or disruption of either the sympathetic or parasympathetic divisions of the ANS. Specific such disorders include autoimmune autonomic ganglionopathy, congenital central hypoventilation syndrome, familiar dysautonomia, Holmes-Adie syndrome, multiple system atrophy, Shy-Drager syndrome, neurally mediated syncope, orthostatic hypotension, postural tachycardia syndrome, striatonigral degeneration, vasovagal syncope and others. By modulating spinal circuits, our tsDCS devices treat autonomic disorders that currently have no effective treatments.

The above described tsDCS teaching, especially including a wearable device, enables convenient and constant wearable stimulation for patients and individuals. In some embodiments, tsDCS is paired with stimulation of a peripheral nerve to an effector organ (e.g., muscle). Applications include modulating muscle tone in skeletal muscle, with surface or implantable electrodes. Implantable electrodes and an implantable tsDCS stimulator embodiment of these teachings enable stimulation of smooth muscle such as that of bladder and bladder sphincters, anal sphincters, visceral organs, airways, heart, digestive organs, glands and other.

The processes and disorders of the ANS listed above can in some instances be modulated more efficiently via an implanted electrode. The implanted electrodes preferably are at the nerve leading to the smooth muscle, striated muscle or at a ganglion or plexus associated with the ANS. This location can be directly at the sympathetic trunk or ganglia, celiac ganglion, superior mesenteric ganglion, inferior mesenteric ganglion, or by applying stimulation at the post-ganglionic nerve. The parasympathetic nervous system has ganglia in close proximity to or located in the organs being innervated, and implantable electrodes can be placed in proximity to these parasympathetic ganglia.

Figure 14:
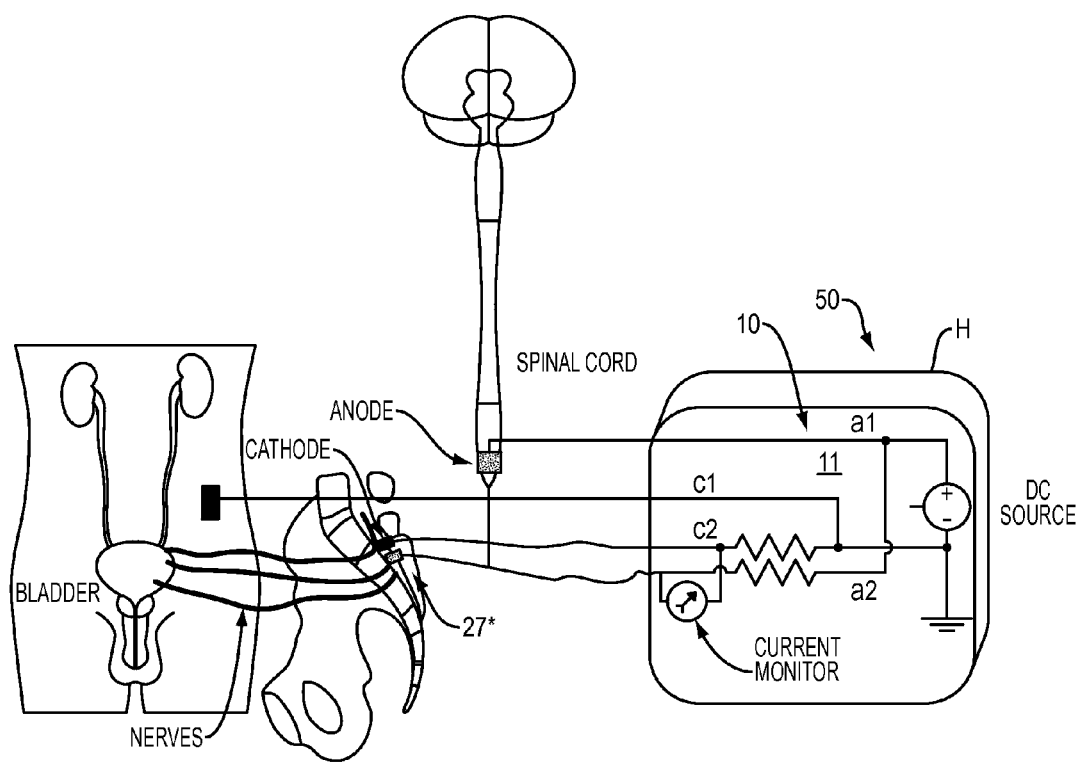
FIG. 14: Shows an illustrative embodiment for treating bladder muscle tone abnormalities in a practice of these teachings providing a stimulation device in a housing as a wearable muscle tone regulator for non-invasive stimulations in practice of embodiments of these teachings, or as an implantable stimulator.

In one embodiment of these teachings, we provide a wearable or implantable system for modulating sacral nerves. Referring to FIG. 14, regulating device 10 is provided as a wearable or implantable regulating device 50, having the tsDCS–pDCS stimulation circuit 11 in a housing H. This would be for use with implantable electrode leads used for stimulation in practice of embodiments of these teachings. This may also include use as an implantable DC stimulator. In practice of these teachings, we can treat flaccid, spastic or rigid conditions by use of an implantable electrode for deep nerves to resolve a need for on-demand, frequent or continuous stimulation.

An illustrative use is shown in FIG. 14 for treating incontinence, such as fecal or urinary, as muscle tone abnormalities. The muscle of the bladder can suffer either from excessive muscle tone or low muscle tone. In either case, a table top, wearable or implantable stimulator of these teachings can be used to up or down regulate that muscle tone. In case of a rigid or spastic bladder problem, the anode would be implanted over the epidural surface of the sacral segments of the spinal cord and an implantable electrode cathode 27* would be implanted over the sacral nerves at the level of S2 to S4 as shown. For low muscle tone (flaccid bladder) the reverse polarities would be used. Device 100 is also provided with a microprocessor with memory 91 in FIG. 9, which enables pre-programmed operation, or responsive remote operation via a communication link 99. Controller circuit 90 monitors the DC source and depending upon direction of the current establishes either anodal-spinal down-regulate mode or the opposite up-regulate mode, and illuminates either a down-regulate indicator 96 or an up-regulate indicator 98 for the reverse, for further assuring safe operation of system 100.

This configuration may be used for urinary control as shown or for fecal control when applied to control the anal sphincter. This configuration may also be used for any other muscle problem that requires specific muscle tone control. Embodiments of these teachings thus enable treatment of humans using a wearable or implantable stimulation system.

Illustrative embodiments of the present teachings are discussed below by way of illustration and are not a limitation of the teachings. This is illustrated with neuromodulation applied to the autonomic nervous system using spinal tsDCS, demonstrating modulation of function by controlled excitation and/or inhibition of neural pathways for treatment of various neurological conditions. This may be accomplished with various devices of the invention, including implantable or wearable devices and/or electrodes.

Modulation of Renal Function

Figure 15:
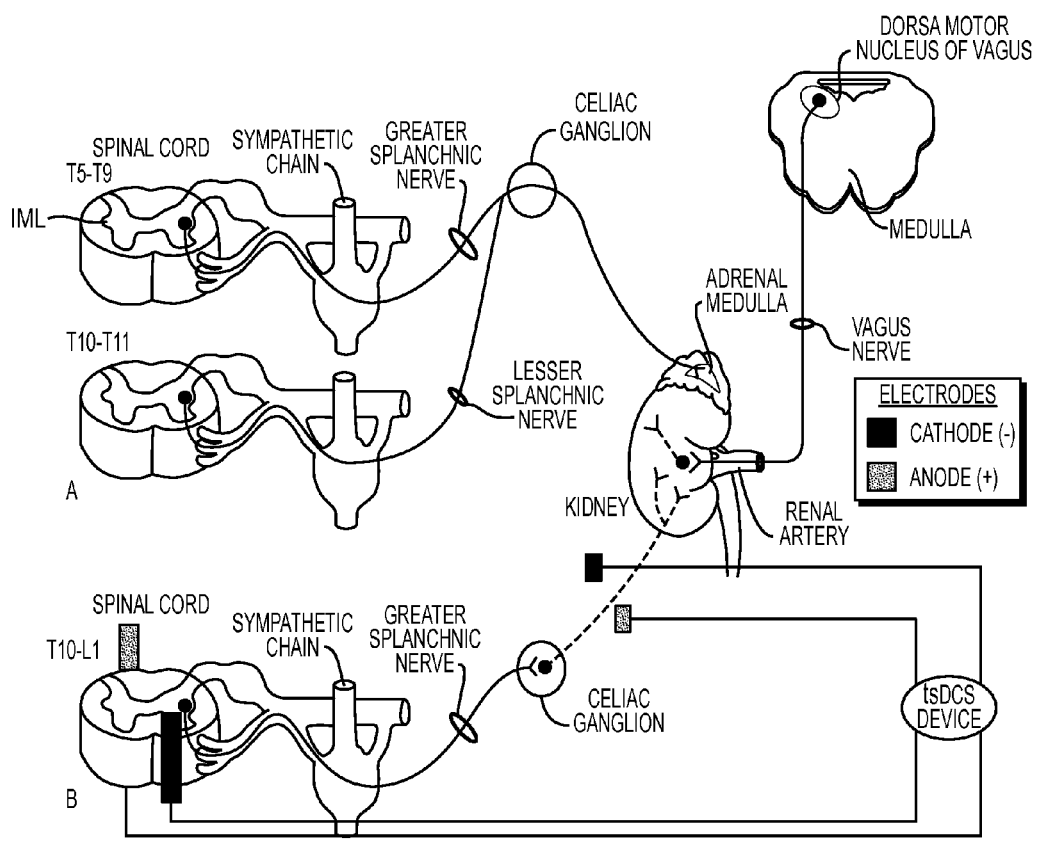
FIG. 15: Shows Neuromodulation strategy for modulating renal function based on decreasing sympathetic tone.

The kidney is responsible for excretion of the products of metabolism and removal of excess water, also having endocrine functions by producing erythropoietin, renin and other factors. Neural control of kidney and adrenal gland is shown in FIG. 15. Sympathetic control is by sympathetic efferents from T10-L1 that run via the sympathetic trunk and the splanchnic nerves to the celiac ganglion and aortiocorenal ganglion. Post-ganglionic fibers contribute to the renal plexus which gives rise to the renal nerves that supply the kidney and its blood vessels, glomeruli and tubules. Stimulation of the renal nerves leads to increased vasoconstriction of the blood vessels supplying the kidney, decreased removal of water and sodium from the blood, and increased renin secretion. Parasympathetic control is from the vagus nerve, which arises from the dorsal motor nucleus of the vagus nerve in the brainstem.

Role in Disease

Poor renal function leads to increased retention of metabolites and water. Toxic metabolites can accumulate, and excess water can lead to hypertension (HTN), congestive heart failure (CHF), obesity and other disorders.

Neuromodulation Strategies Based on tsDCS to Treat Renal Dysfunction

Decrease sympathetic tone—A decrease in sympathetic tone results in decreased retention of water and sodium. In an embodiment of the present teachings, this is achieved by applying modal tsDCS with cathodal and modal electrodes applied at the spinal level of T10-L1 as shown in FIG. 15. In a further embodiment, this is augmented with electrical inhibition of the renal nerves using implanted neural electrodes, and in one embodiment further including respective cathodal and anodal neural electrodes applied as shown in FIG. 15. Such an approach can be used to treat HTN, CHF, obesity and other disorders.

Increase parasympathetic tone—An increase in parasympathetic tone results in decreased retention of water and sodium. To achieve this in practice of an embodiment of these teachings, cathodal tsDCS is applied at the level of the dorsal motor nucleus of the vagus nerve in the brainstem and electrical stimulation is applied to the pre-ganglionic fibers of the vagus nerve using implanted electrodes, as shown in FIG. 13. Cathodal tsDC to the vagal nucleus in this embodiment is applied with electrodes at T1-T2 and at the cranial apex. Alternatively in this embodiment, cathodal tsDCS to the vagal nucleus is applied with electrodes applied bilaterally to the mastoid processes of the skull. Such an approach could be used to treat HTN, CHF, obesity and other diseases.

Figure 16:
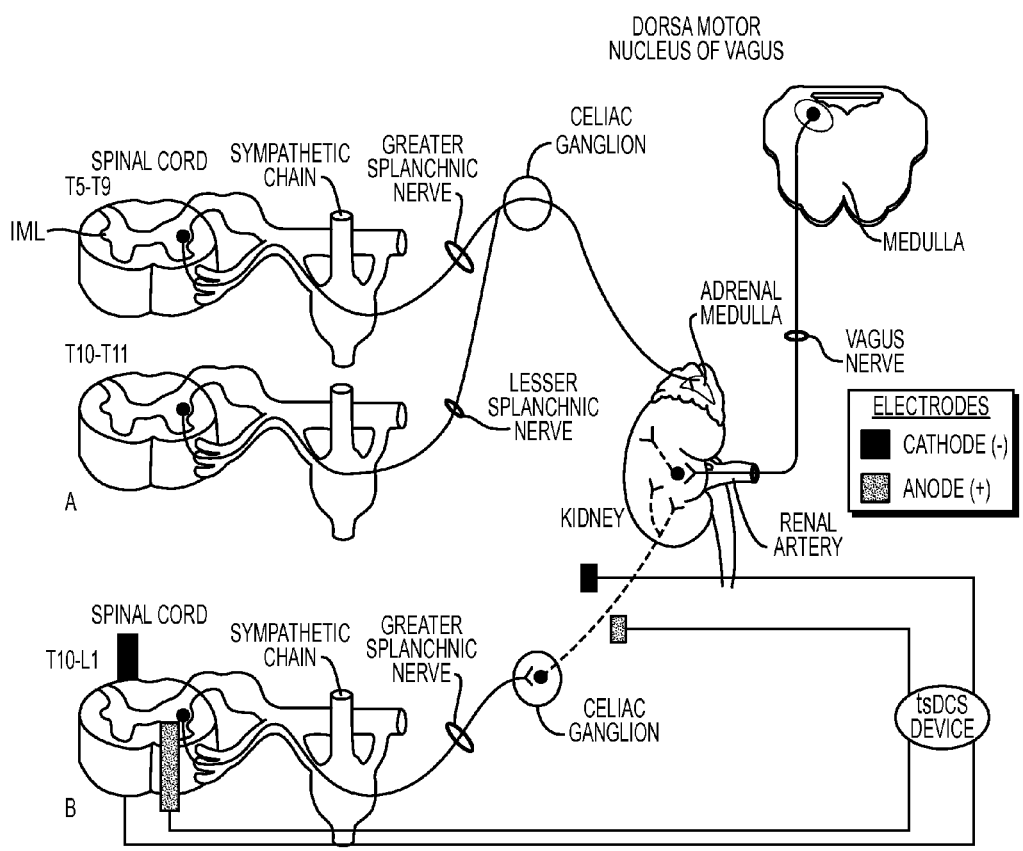
FIG. 16: Shows Neuromodulation strategy for modulating renal function based on increasing sympathetic tone.

Increase sympathetic tone—An increase in sympathetic tone results in increased retention of water and sodium. In an embodiment of the present teachings, this is achieved by cathodal tsDCS with cathodal and anodal electrodes applied at the spinal level of T10-L1 as shown in FIG. 16. In a further embodiment, this is augmented with electrical stimulation of the renal nerves using implanted neural electrodes, and in one embodiment further including respective cathodal and anodal neural electrodes applied as shown in FIG. 16.

Modulation of Bladder Function

Figure 17:
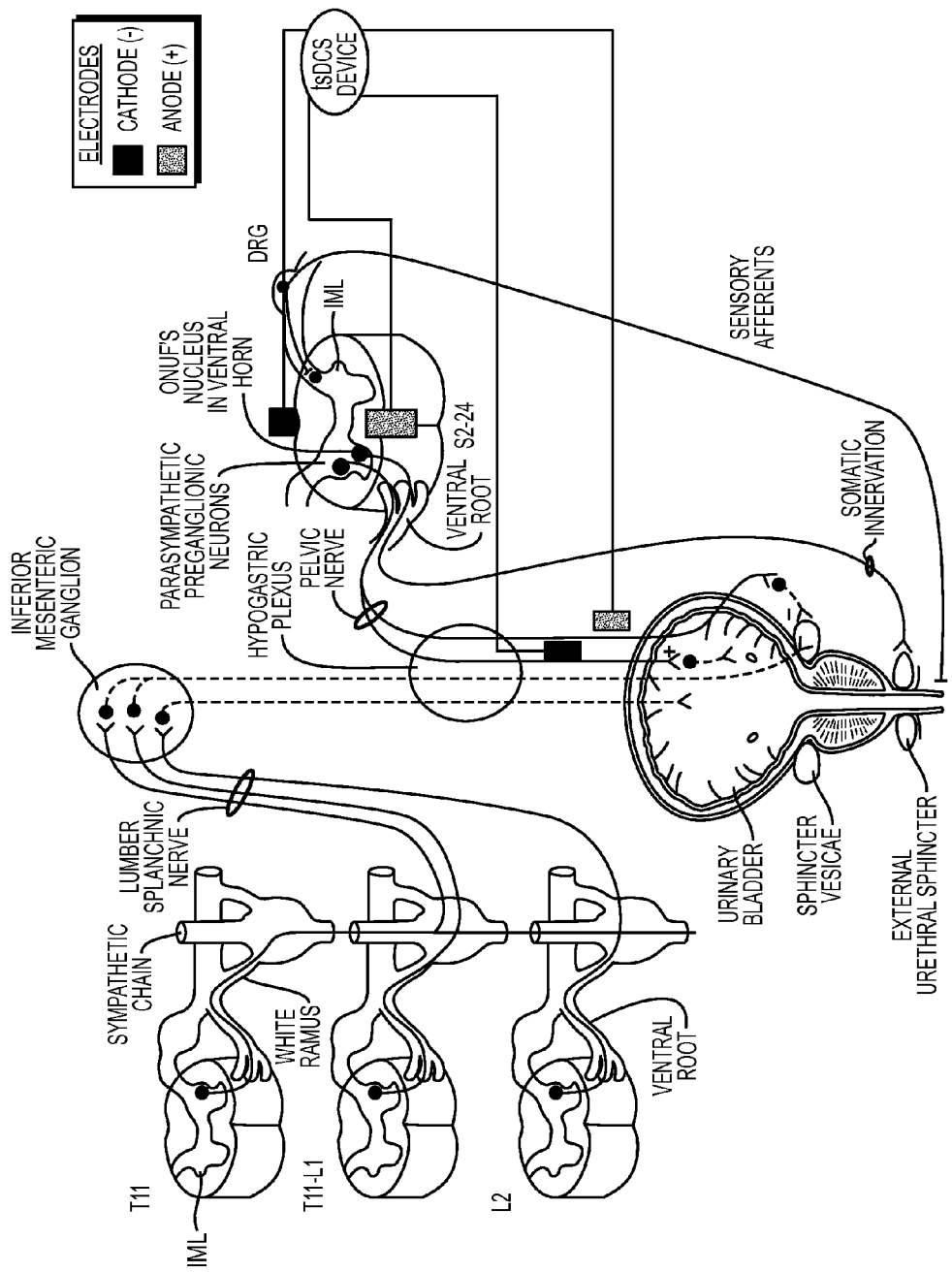
FIG. 17: Shows Neuromodulation strategy for treating urinary retention based on increasing parasympathetic tone.

The bladder functions as a reservoir and is responsible for storing urine that has been formed by the kidneys in the process of eliminating metabolites and excess water from the blood. The stored urine is released via the urethra in the process of micturition. Referring to FIG. 17, sympathetic control is from sympathetic efferents from T11-L2 that run via the sympathetic trunk and the splanchnic nerves to the inferior mesenteric ganglion. Post-ganglionic fibers contribute to the hypogastric plexus and reach the bladder where they synapse on the detrusor muscle, and also synapse on the sphincter vesicae at the bladder neck. Parasympathetic control is from parasympathetic fibers that arise from S2-S4 and travel via the pelvic splanchnic nerves to synapse on post-ganglionic neurons located in a dense plexus among the detrusor smooth muscle cells in the wall of the bladder. Post-ganglionic parasympathetic fibers cause contraction of the bladder detrusor muscle and relaxation of the sphincter vesicae. The external urethral sphincter (EUS) consists of striated muscle and is under voluntary control via alpha motor neurons in Onuf's nucleus in the ventral horns of S2-S4. Afferent responses from bladder stretch receptors enter the spinal cord at T11-L2 and also S2-S4 where they travel up to brainstem areas. Sensory fibers in the urethral wall respond to urinary flow by causing firing of their cell bodies located in dorsal root ganglia, which synapse on neurons in the spinal cord dorsal horn. These sensory fibers travel to the spinal cord via the pudendal nerve, and transection of this sensory nerve reduces bladder contraction strength and voiding efficiency.

Role in Disease

Urinary retention is an inability to empty the bladder completely and can be acute or chronic. Retention can be due to numerous issues, including constipation, prostatic enlargement, urethral strictures, urinary tract stones, tumors, and nerve conduction problems. Such nerve conduction problems are seen in brain and spinal cord injuries, diabetes, multiple sclerosis, stroke, pelvic surgery, heavy metal poisoning, aging and idiopathically. These result in either weak bladder contraction and/or excess sphincter activation. As such, modulation strategies that enable improved emptying of the bladder are of therapeutic interest.

Urinary incontinence is loss of bladder control leading to mild leaking all the way up to uncontrollable wetting. It results from weak sphincter muscles, overactive bladder muscles, damage to nerves that control the bladder from diseases such as multiple sclerosis and Parkinson's disease, and can occur after prostate surgery. As such, modulation strategies that treat urinary incontinence are of therapeutic interest.

Neuromodulation Strategies Based on tsDCS to Treat Urinary Retention

Increase parasympathetic tone—An increase in parasympathetic tone results in increased bladder contraction and relaxation of the sphincter vesicae. In an embodiment of the present teachings, this is achieved by applying cathodal tsDCS with cathodal and anodal electrodes applied at the spinal level of S2-S4 as shown in FIG. 17. In a further embodiment, this is augmented with electrical excitation of the parasympathetic preganglionic fibers in pelvic nerve using implanted neural electrodes, and in one embodiment further including respective cathodal and anodal neural electrodes applied as shown in FIG. 17.

Figure 18:
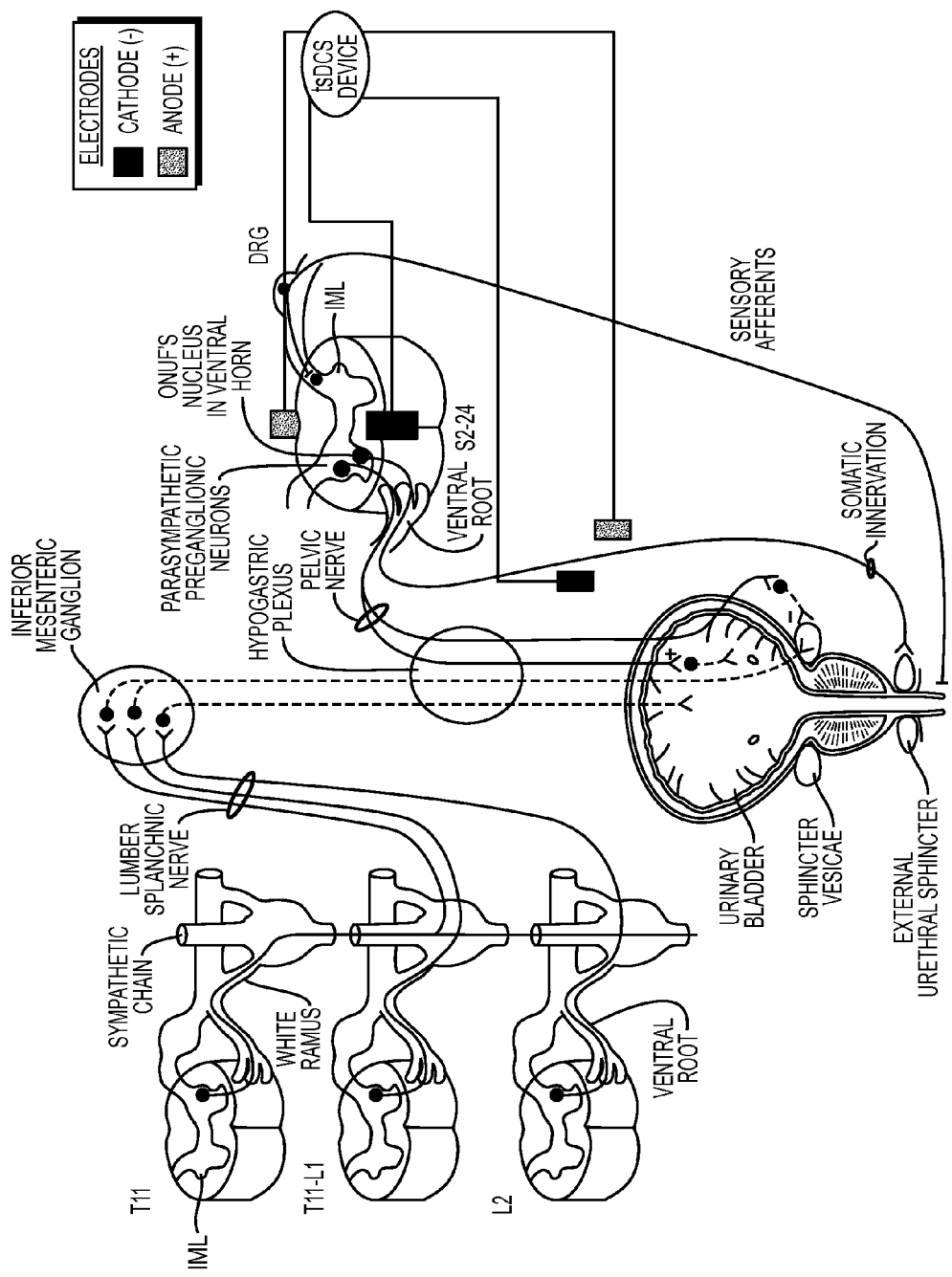
FIG. 18: Shows Neuromodulation strategy for treating urinary retention based on inhibiting somatic efferents.

Inhibit somatic efferents—Excessive activity in the somatic efferents innervating the striated muscle of the EUS results in contraction of the sphincter. In an embodiment of the present teachings, this is achieved by applying modal tsDCS with cathodal and anodal electrodes applied at the spinal level of S2-S4 as shown in FIG. 18. In a further embodiment, this is augmented with electrical inhibition of the pudendal nerve using implanted neural electrodes, and in one embodiment further including respective cathodal and anodal neural electrodes applied as shown in FIG. 18.

Figure 19:
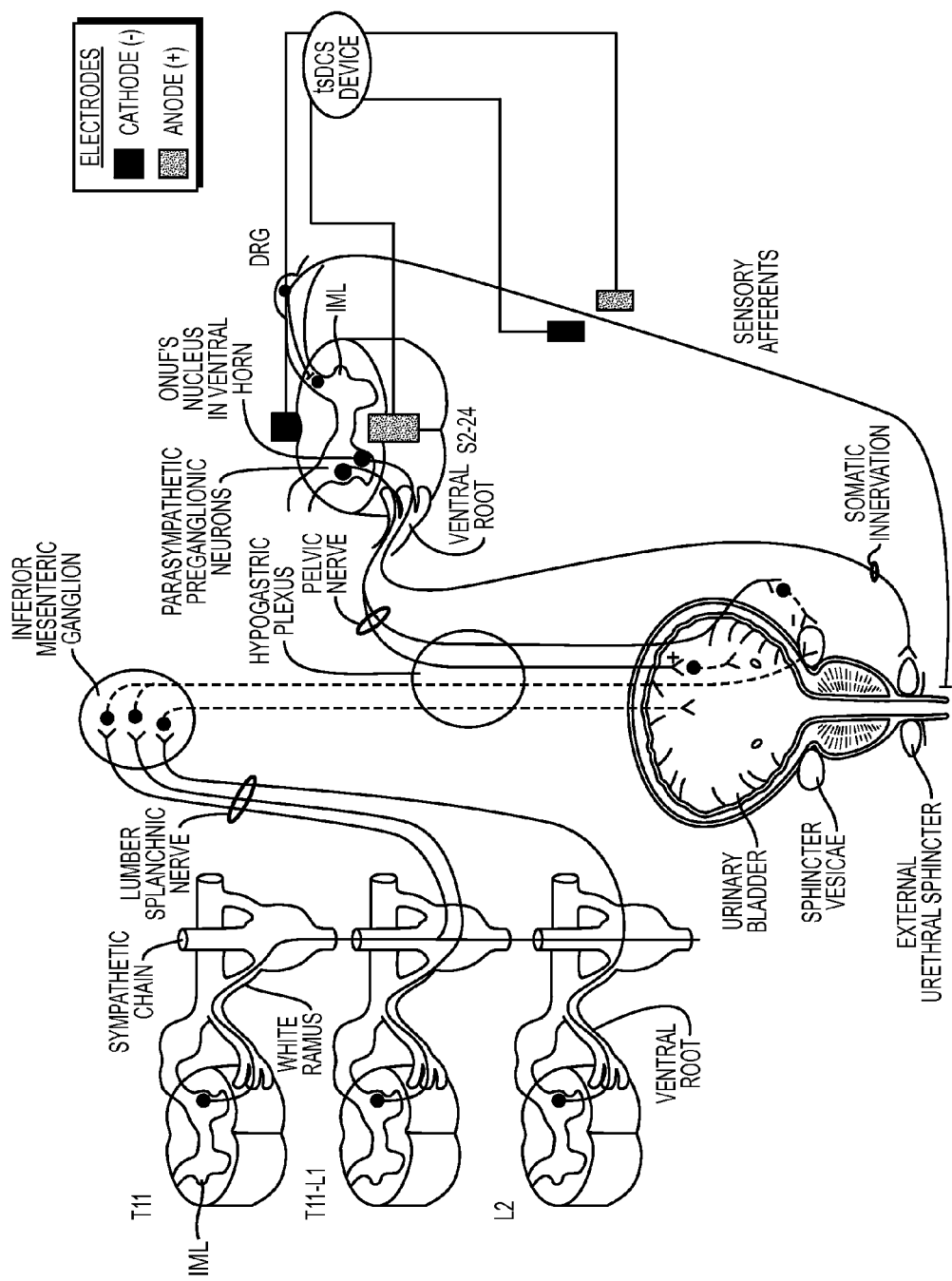
FIG. 19: Shows Neuromodulation strategy for treating urinary retention based on stimulating sensory afferents.

Stimulate sensory afferents—Stimulation of the sensory afferents that fire in response to urine flow through urethra results in increased strength of bladder contraction and voiding efficiency. In an embodiment of the present teachings, this is achieved by applying cathodal tsDCS with cathodal and anodal electrodes applied at the spinal level of S2-S4 as shown in FIG. 19. In a further embodiment, this is augmented with electrical excitation of the pudendal nerve using implanted neural electrodes, and in one embodiment further including respective cathodal and anodal neural electrodes applied as shown in FIG. 19.

Neuromodulation Strategies Based on tsDCS to Treat Urinary Incontinence

Figure 20:
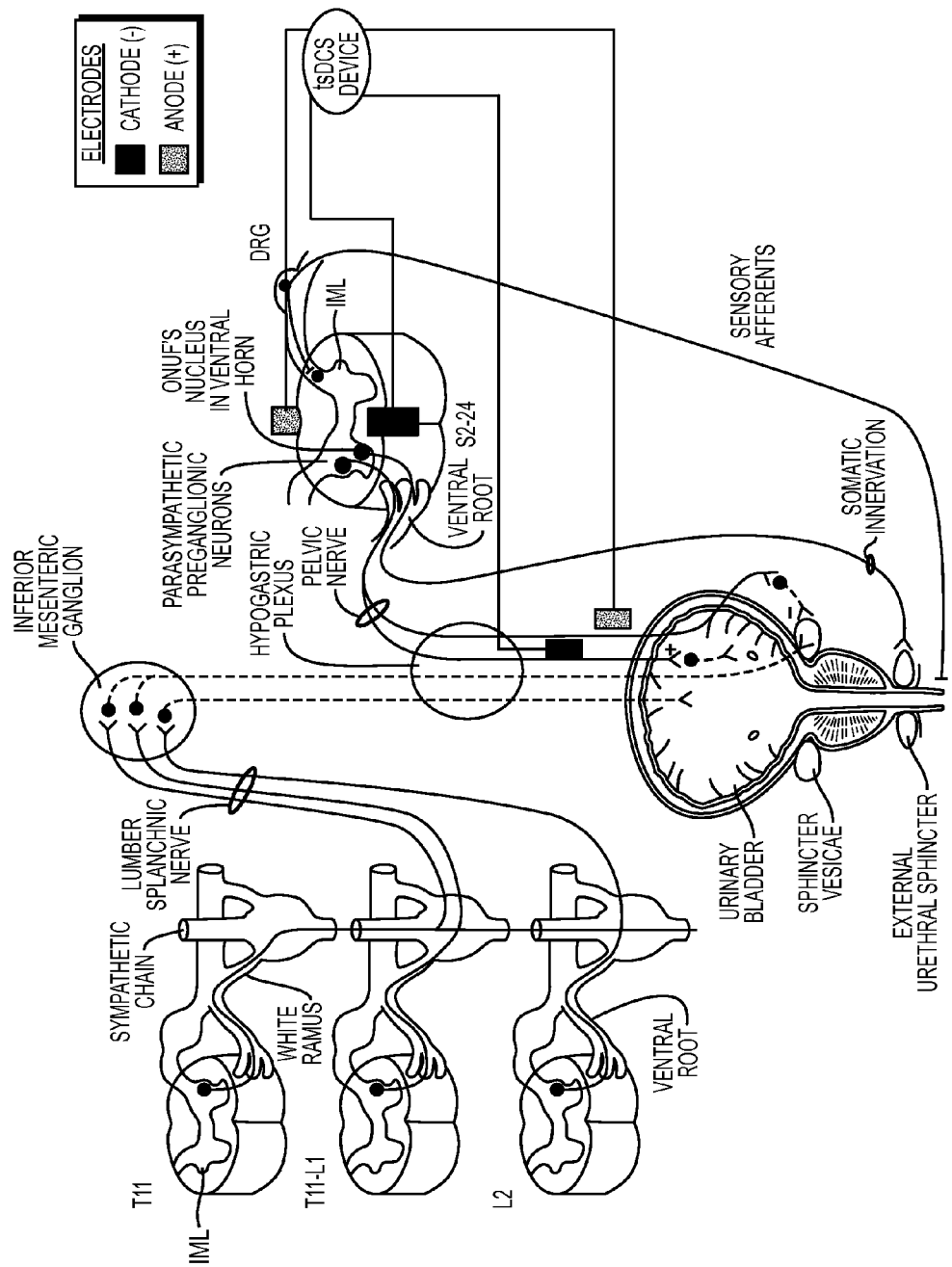
FIG. 20: Shows Neuromodulation strategy for treating urinary incontinence based on decreasing parasympathetic tone.

Decrease parasympathetic tone—A decrease in parasympathetic tone would result in relaxation of bladder contraction and contraction of the sphincter vesicae. In an embodiment of the present teachings, this is achieved by applying anodal tsDCS with cathodal and anodal electrodes applied at the spinal level of S2-S4 as shown in FIG. 20. In a further embodiment, this is augmented with electrical inhibition of the parasympathetic preganglionic fibers in pelvic splanchnic nerves using implanted electrodes, and in one embodiment further including respective cathodal and anodal neural electrodes applied as shown in FIG. 20.

Figure 21:
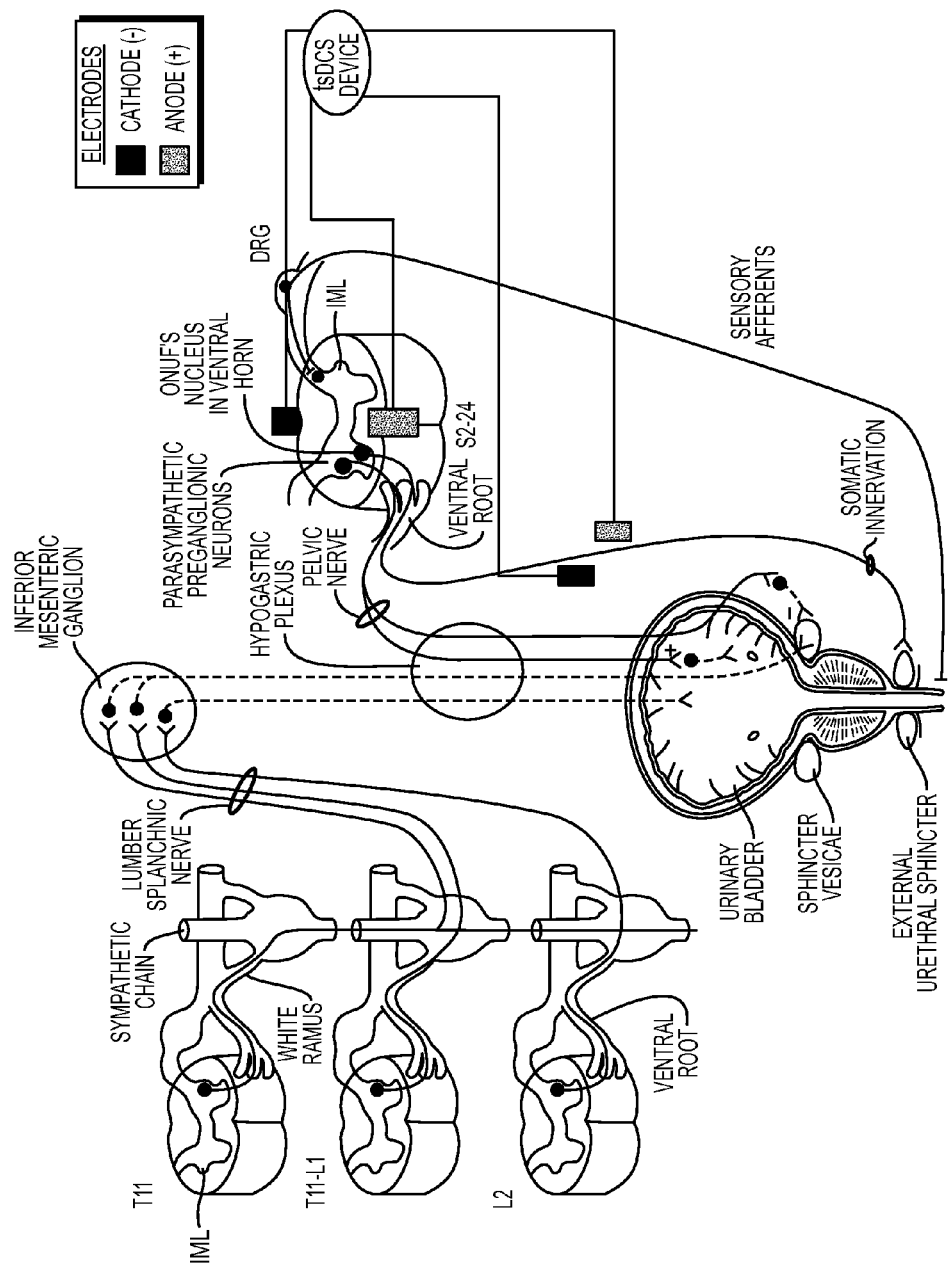
FIG. 21: Shows Neuromodulation strategy for treating urinary incontinence based on stimulating somatic efferents.

Stimulate somatic efferents—Insufficient activation of the somatic efferents innervating the striated muscle of the EUS results in weak contraction of this sphincter muscle. In an embodiment of the present teachings, this is achieved by applying cathodal tsDCS with cathodal and anodal electrodes applied at the spinal level of S2-S4 as shown in FIG. 21. In a further embodiment, this is augmented with electrical excitation of the pudendal nerve using implanted electrodes, and in one embodiment further including respective cathodal and anodal neural electrodes applied as shown in FIG. 21.

Modulation of Gastrointestinal System Function

The gastrointestinal (GI) system is responsible for digesting our food. The GI system is a series of hollow organs joined in a long tube going from mouth to anus, and includes the esophagus, stomach, small intestines, large intestines and rectum. The liver, pancreas and gallbladder are solid organs of the digestive system. Proper functioning of these hollow organs, together with the enzymes and molecules produced by these solid organs, and the collection of microrganisms colonizing the GI system referred to as the microbiome, is critical for processing, digestion and elimination of foodstuffs. Sympathetic control of the stomach, small intestines and large intestines is by sympathetic efferents from T6-L2 that traverse the sympathetic trunk and the splanchnic nerves (greater, lesser, least and lumbar splanchnics) to reach a network of three ganglia. These ganglia are the celiac ganglion, superior mesenteric ganglion (SMG) and the inferior mesenteric ganglion (IMG), which contain the cell bodies of post-ganglionic sympathetic neurons. Post-ganglionic fibers emerging from the celiac ganglion innervate smooth muscle and glands of the stomach and small intestines, fibers from the SMG innervate distal portions of small intestines, and the ascending and transverse colon, and fibers from the IMG traverse the hypogastric plexus to innervate the transverse colon, descending colon and rectum. Stimulation of the sympathetic nerves to the GI system results in inhibition of peristalsis, contraction of sphincters, and inhibition of secretions from glands. Parasympathetic control of the stomach, small intestines, ascending colon and transverse colon is from the vagus nerve, while parasympathetic control of the distal transverse colon, descending colon and rectum is from S2-S4. Cell bodies of parasympathetic neurons located in the ventral horns of S2-S4 send fibers through the pelvic nerves to post-ganglionic neurons located in Auerbach's (myenteric) and Meissner's (submucosal) plexuses. These post-ganglionic neurons synapse on the smooth muscle and glands of the gastrointestinal tract they innervate. Stimulation of the parasympathetic system results in peristalsis, secretion from glands, and relaxation of sphincters, leading to increased GI motility.

Role in Disease

GI motility disorders are due to either decreased or increased motility, a term used to describe the contraction of the muscles that mix and propel contents in the GI tract. These include disorders such as chronic intestinal pseudo-obstruction, irritable bowel syndrome, constipation, gastroesophageal reflux disease, dumping syndrome, intestinal dysmotility, diabetic gastroparesis, Hirschsprung's disease, gastroparesis, achalasia, small bowel bacterial overgrowth, diarrhea, functional heartburn, functional dysphagia, functional dyspepsia, post-prandial distress syndrome, epigastric pain syndrome, aerophagia, functional vomiting, chronic idiopathic nausea, functional bloating, functional abdominal pain disorder, functional sphincter of Oddi disorder, and other functional disorders. Beyond motility disorders, inflammatory immune-mediated disorders such as Crohn's disease and ulcerative colitis also have mechanisms that are responsive to autonomic control.

Neuromodulation Strategies Based on tsDCS to Increase GI Motility

Figure 22:
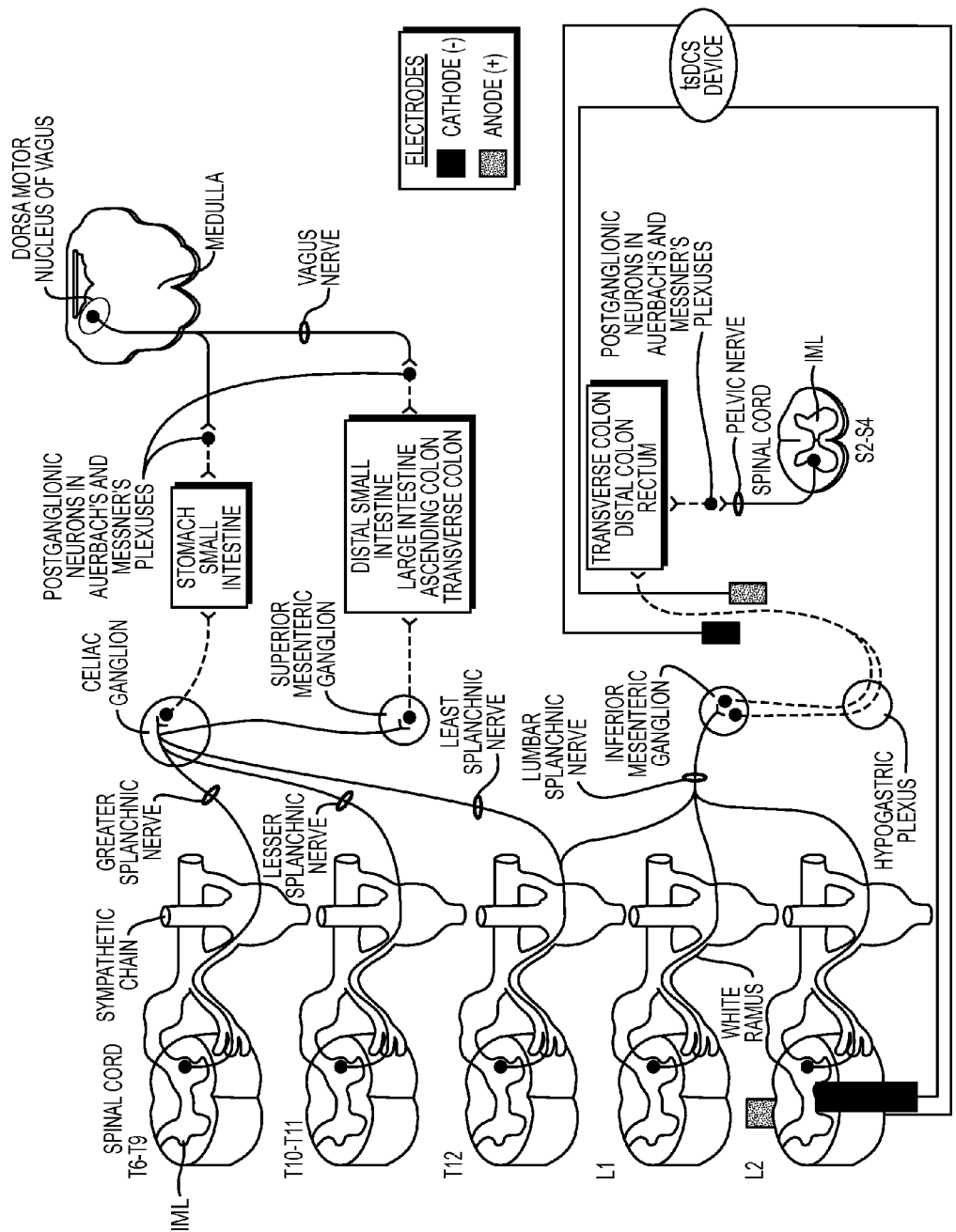
FIG. 22: Shows Neuromodulation strategy for increasing GI peristalsis and secretions based on decreasing sympathetic tone, tsDCS shown only at L2 level but extends across all relevant spinal levels of effector organ being targeted. Stimulation of post-ganglionic fibers shown only distal to hypogastric plexus, but alternatively includes fibers distal to the celiac ganglion and SMG.

Decrease sympathetic tone—A decrease in sympathetic tone results in increased peristalsis and secretion, In an embodiment of the present teachings, increased motility is achieved by applying anodal tsDCS with cathodal and anodal electrodes applied at the spinal level of T6-1,2 as shown in FIG. 22. In a further embodiment, this is augmented with electrical inhibition of the post-ganglionic nerve fibers distal to the celiac ganglion, SMG and IMG, using implanted electrodes, and in one embodiment further including respective cathodal and anodal neural electrodes applied as shown in FIG. 22.

Figure 23:
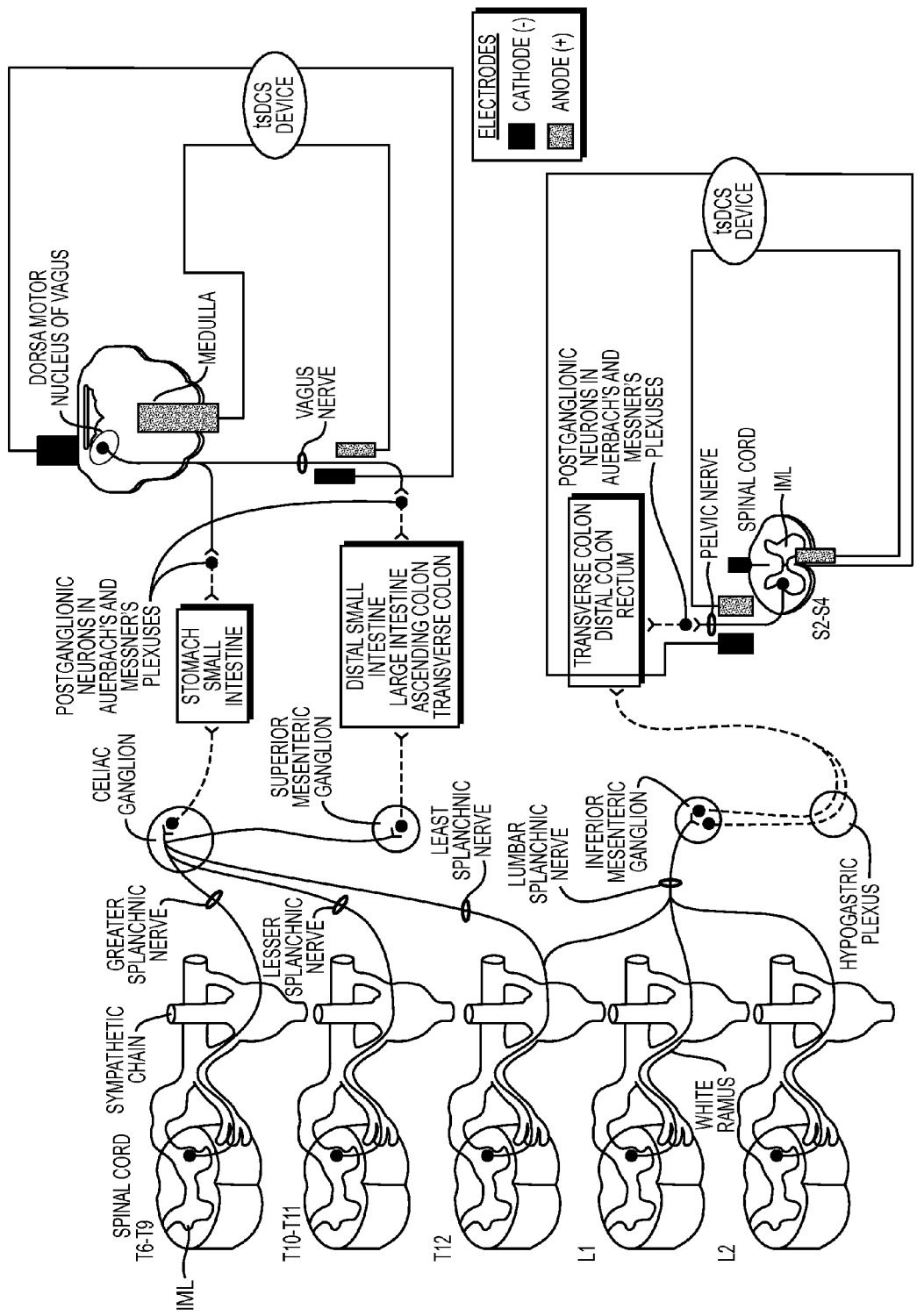
FIG. 23: Shows Neuromodulation strategy for increasing GI peristalsis and secretions based on increasing parasympathetic tone.

Increase parasympathetic tone—An increase in parasympathetic tone results in increased peristalsis and secretion. In an embodiment of the present teachings, increased motility is achieved by applying cathodal tsDCS with cathodal and anodal electrodes applied at the spinal level of S2-S4 as shown in FIG. 23. In a further embodiment, this is augmented with electrical excitation of the pre-ganglionic pelvic nerves using implanted neural electrodes, and in one embodiment further including respective cathodal and anodal neural electrodes applied as shown in FIG. 23. This can be combined with stimulation of the parasympathetic system emanating from the vagus nerve and innervating the stomach, small intestines, proximal large intestines and spleen, as well as the kidneys, liver and heart. To achieve this in practice of an embodiment of the present teachings, cathodal tsDCS is applied at the level of the dorsal motor nucleus of the vagus nerve in the brainstem and electrical stimulation is applied to the pre-ganglionic fibers of the vagus nerve using implanted electrodes. Cathodal tsDC to the vagal nucleus in this embodiment is applied with electrodes at T1-T2 and at the cranial apex. Alternatively in this embodiment, cathodal tsDCS to the vagal nucleus is applied with electrodes applied bilaterally on the mastoid process.

Neuromodulation Strategies Based on tsDCS to Decrease GE Motility

Increase sympathetic tone—An increase in sympathetic tone results in decreased peristalsis and secretion. In an embodiment of the present teachings, this decreased motility is achieved by applying cathodal tsDCS with cathodal and anodal electrodes applied at the spinal level of T6-L2. In a further embodiment, this is augmented with electrical excitation of the post-ganglionic nerve fibers in and distal to the hypogastric plexus using implanted neural electrodes, and in one embodiment further including respective cathodal and anodal neural electrodes in practice of the invention.

Decrease parasympathetic tone—A decrease in parasympathetic tone results in diminished peristalsis and secretion. In an embodiment of the present teachings, this decreased motility is achieved by applying anodal tsDCS with cathodal and anodal electrodes applied at the spinal level of S2-S4. In a further embodiment, this is augmented with electrical inhibition of the pre-ganglionic pelvic nerves using implanted neural electrodes, and in one embodiment further including respective cathodal and anodal neural electrodes in practice of these teachings.

Modulation of Anal Sphincter Function

The anal sphincters are responsible for maintaining control over rectal contents. Sympathetic outflow is from L1-L2, with pre-ganglionic fibers traversing the sympathetic chain and synapsing on post-ganglionic neurons in the IMG. Post-ganglionic sympathetic fibers run via the hypogastric nerve, hypogastric plexus and pelvic nerves to innervate the internal anal sphincter (IAS). Sympathetic stimulation maintains IAS contraction. The internal anal sphincter receives parasympathetic supply from S2-S4 outflow, and its contraction is inhibited by parasympathetic fiber stimulation. The striated sphincter muscles (external anal sphincter and puborectalis muscle) are under voluntary control and are innervated by somatic efferent fibers traveling in the pudendal nerve (S2-S4).

Role in Disease

Dysfunction of the anal sphincter leads to fecal incontinence, which results in leakage or inability to retain gas and/or solid feces. It results from weak or damaged sphincter muscles, and damage to nerves that control the sphincters from disorders such as multiple sclerosis, Parkinson's disease, spinal cord injury, brain injury and stroke. As such, modulation strategies that treat fecal incontinence are of significant therapeutic interest.

Neuromodulation Strategies Based on tsDCS to Treat Fecal Incontinence

Figure 24:
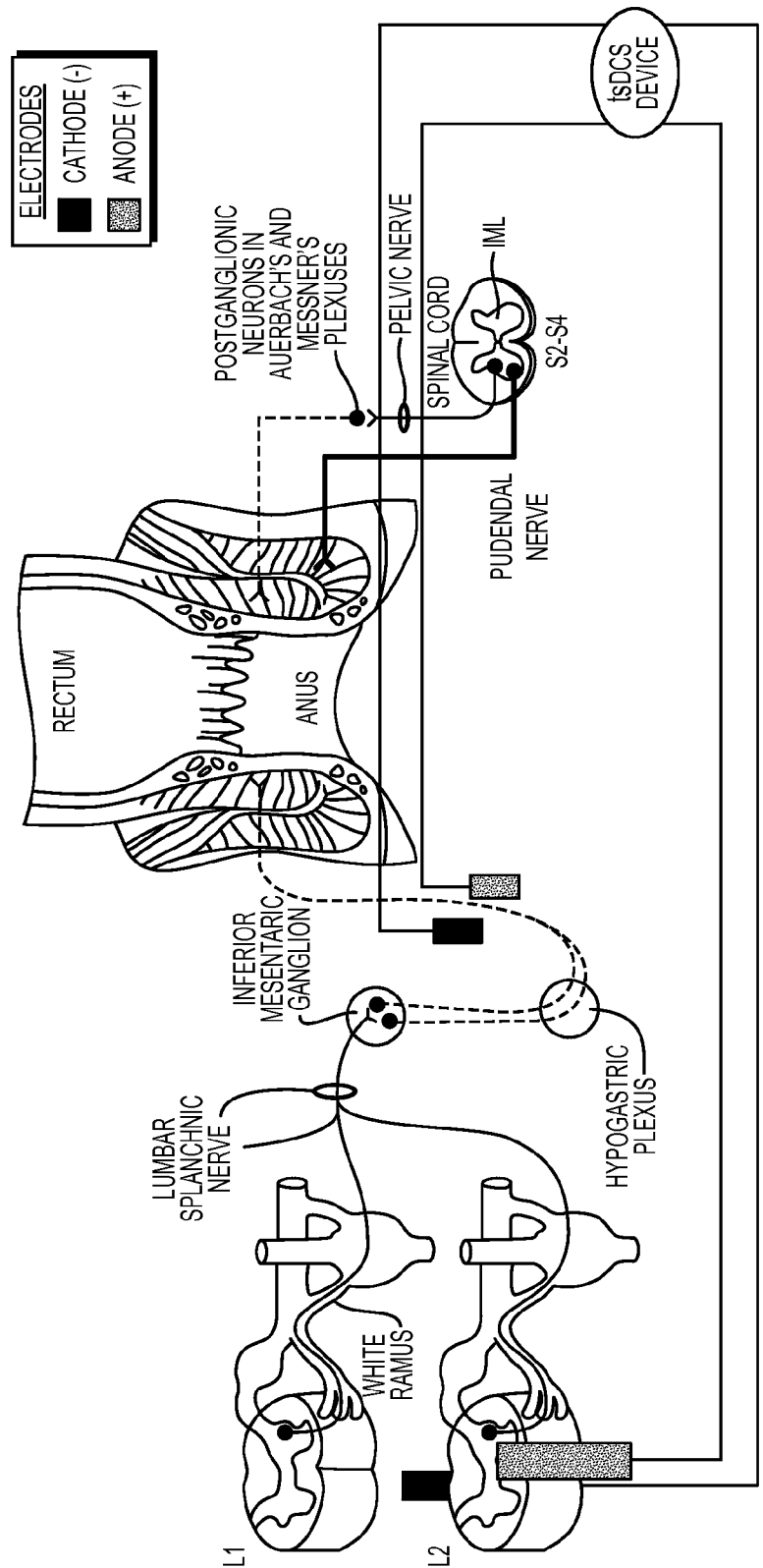
FIG. 24: Shows Neuromodulation strategy for treating fecal incontinence based on increasing sympathetic tone.

Increase sympathetic tone—An increase in sympathetic tone results in increased contraction of the IAS. In an embodiment of the present teachings, increased IAS contraction is achieved by applying cathodal tsDCS with cathodal and anodal electrodes applied at the spinal level of L1-L2 as shown in FIG. 24. In a further embodiment, this is augmented with electrical excitation is applied to the post-hypogastric plexus pelvic nerves using implanted neural electrodes, and in one embodiment further including respective cathodal and anodal neural electrodes applied as shown in FIG. 24.

Figure 25:
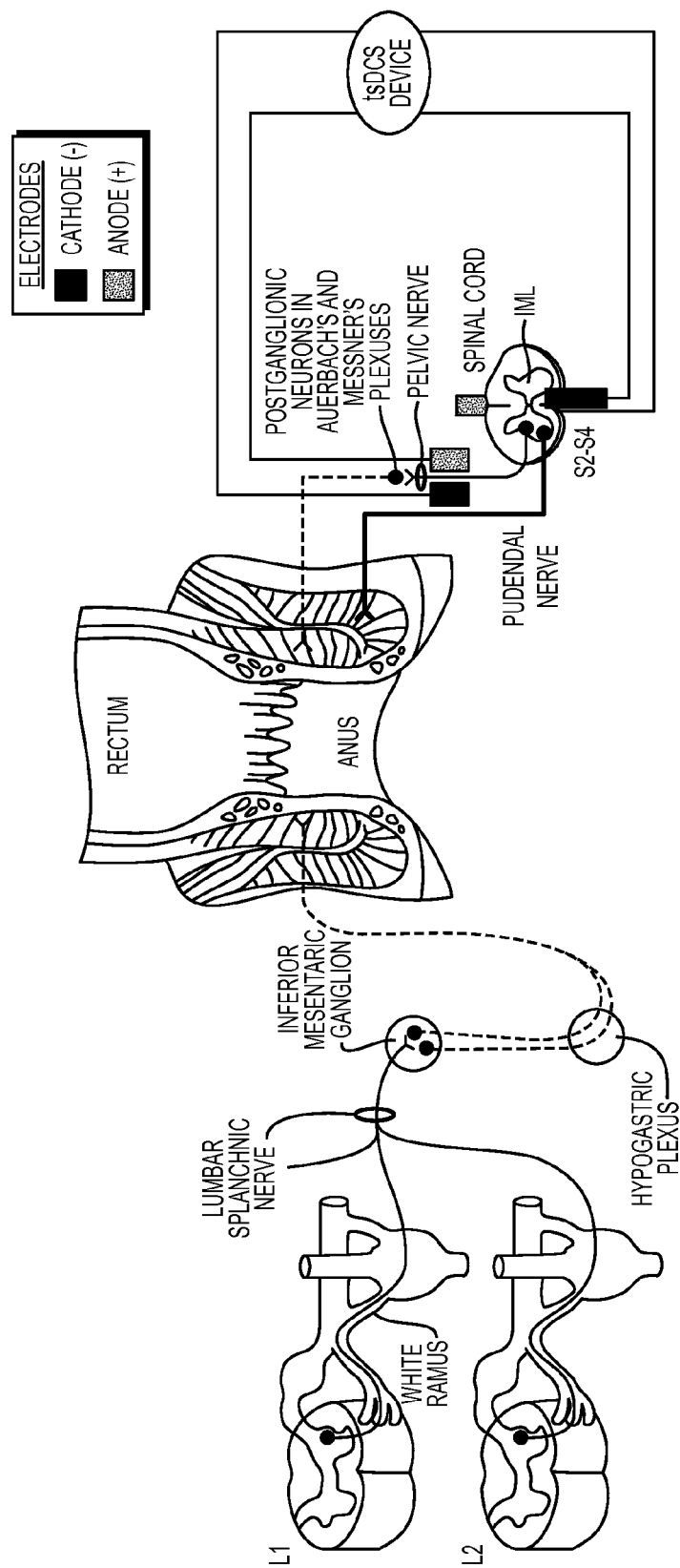
FIG. 25: Shows Neuromodulation strategy for treating fecal incontinence based on decreasing parasympathetic tone.

Decrease parasympathetic tone—A decrease in parasympathetic tone results in lesser relaxation of IAS, enabling the IAS to stay more contracted. This greater contraction of IAS is achieved in an embodiment of the present teachings by applying anodal tsDCS with cathodal and anodal electrodes applied at the spinal level of S2-S4 as shown in FIG. 25. In a further embodiment, this is augmented with electrical inhibition of the parasympathetic preganglionic fibers in pelvic splanchnic nerves applied using implanted neural electrodes, and in one embodiment further including respective cathodal and anodal neural electrodes applied as shown in FIG. 25.

Figure 26:
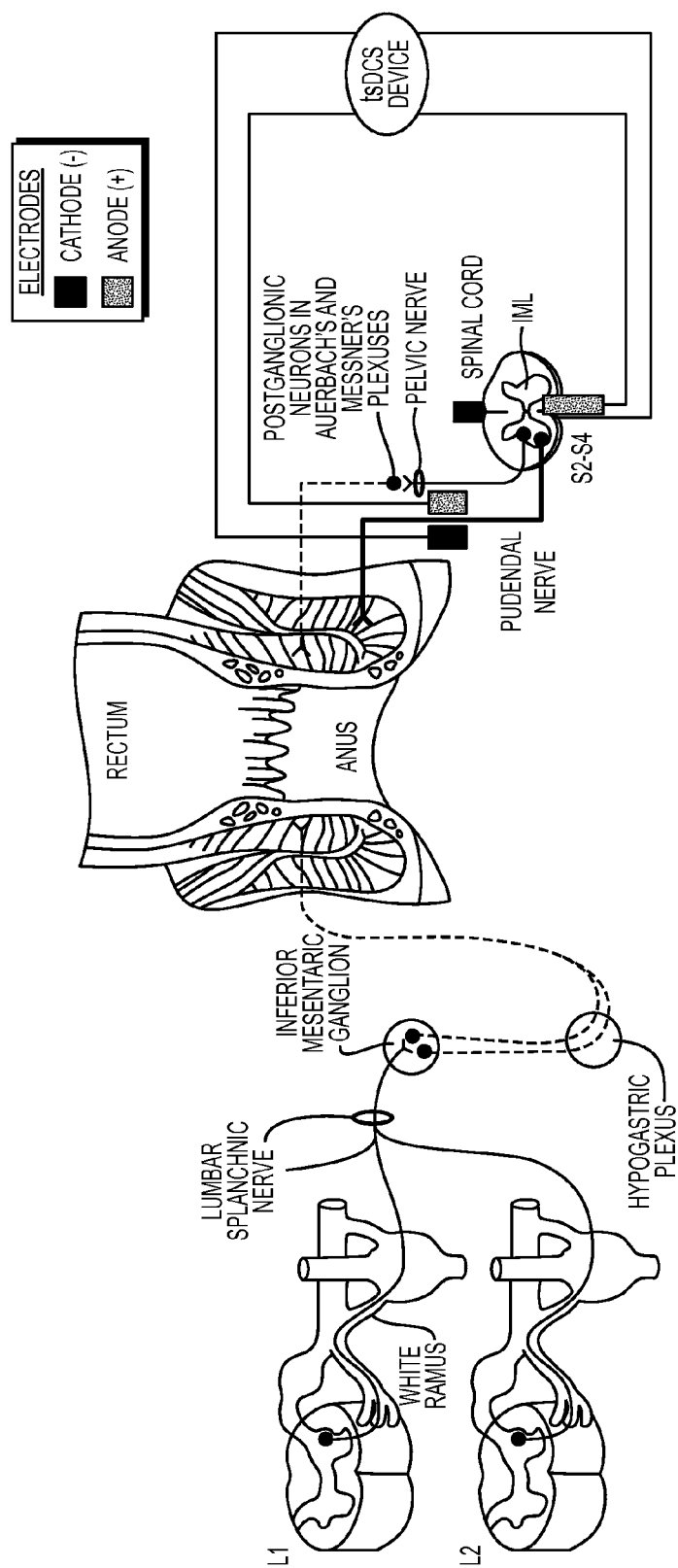
FIG. 26: Shows Neuromodulation strategy for treating fecal incontinence based on stimulating somatic efferents.

Stimulate somatic efferents—Insufficient activation of the somatic efferents innervating the striated muscle of the external sphincter results in weak contraction of this sphincter muscle. To achieve greater contraction of the external sphincter muscle in practice of an embodiment of the present teachings, cathodal tsDCS is applied at the level of S2-S4 with cathodal and anodal electrodes applied as shown in FIG. 26. In a further embodiment, this is augmented with electrical excitation of the pudendal nerve applied using implanted neural electrodes, and in one embodiment further including respective cathodal and anodal neural electrodes applied as shown in FIG. 26.

It will be appreciated that embodiments of the present teachings feature tsDCS spinal stimulation. In many embodiments, this tsDCS stimulation is augmented with a neural stimulation. In practices of these teachings, peripheral pDCS is continuous, non-varying, steady-state direct current stimulation, while in other embodiments, stimulation of a peripheral nerve or autonomic nerve fiber associated with an effector organ may include pulsed electrical stimulation, functional electrical stimulation, continuous DCS, pulsed DCS, or other alternating signals. The present teachings also may be practiced with wireless microstimulators (see, for example, U.S. Pat. No. 5,193,539, A Programmable Implantable Microstimulator SoC, IEEE TRANSACTIONS ON BIOMEDICAL CIRCUITS AND SYSTEMS, VOL. 5, NO. 6, DECEMBER 2011, both of which are incorporated by reference herein in their entirety and for all purposes) with Wireless Telemetry, micro-coil magnetic stimulation (see, for example, Magnetic Stimulation of Subthalamic Nucleus Neurons using Micro-coils for Deep Brain Stimulation, 6th Annual International IEEE EMBS Conference on Neural Engineering San Diego, Calif., 6-8 Nov. 2013, which is incorporated by reference here in a its entirety and for all purposes) and the like.

In one embodiment of the present teachings, peripheral stimulation is continuous steady-state and non-varying. In another embodiment of the invention, excitation or inhibition of a stimulated autonomic nerve fiber depends on the frequency of the applied electrical stimulation. In one illustrative but non-limiting practice of the invention, inhibition of parasympathetic fibers is achieved with high-frequency electrical stimulation (greater than about 50-400 Hz), while excitation of parasympathetic fibers is achieved with low-frequency electrical stimulation (less than about 50-400 Hz). Similarly, inhibition of sympathetic fibers is achieved with high-frequency electrical stimulation (greater than about 50-400 Hz), while excitation of sympathetic fibers is achieved with low-frequency electrical stimulation (less than about 50-400 Hz).

In yet another embodiment of the present teachings, a series of implanted electrode leads for stimulation of multiple nerves leading to multiple organs is provided. For example, one useful constellation of functions to modulate for a specific scenario includes increasing airway bronchodilation, increasing adrenal gland production of adrenergic hormones, and increasing hepatic glucose production and release in anticipation of an intense burst of physical activity. Brain signals to the sympathetic nervous system traversing the spinal cord are amplified by the wearable tsDCS device, which may also stimulate multiple nerves involved in multiple functions. As such, a neuromodulatory approach to the amplification of the "fight-or-flight" response is enabled.

In embodiments of the present teachings, the tsDCS device is fully implantable, with electrode leads from the device to dorsal spinal location and ventral location tunneled subcutaneously. Electrode leads from the tsDCS device which function for peripheral stimulation are also tunneled subcutaneously with electrodes implanted on the appropriate nerves of the effector organ being modulated. In another embodiment, the tsDCS device remains external to the body and wearable, but has electrode leads for peripheral stimulation that are either surface mounted or implanted.

In another embodiment of the present teachings, a wearable tsDCS unit that wirelessly controls an implanted stimulator is combined with a sensor that detects a relevant physiological state to form a closed-loop system. The wearable tsDCS unit wirelessly communicates with the sensor, which could be either implanted or wearable, and activates tsDCS spinal stimulation and stimulation of an effector organ via the implanted stimulator, when it detects a relevant state. The sensor can be configured to detect blood pressure, heart rate, body temperature, respiration rate, skin turgor, skin conductivity, oxygenation state, bladder pressure, urine osmolarity, hemodynamic parameters, specific cardiac rhythms by EKG, urethral pressure, anal sphincter pressure, muscle contraction state by EMG, specific brain waves by EEG, electrolytes, specific proteins and signaling molecules in specific tissue compartments, blood glucose concentration, gastric pH, gastrointestinal motility sounds, environmental cues such as specific sights, sounds and signals, and other parameters depending on intended application. The neuromodulation system is thus activated upon sensing a specific state, and inactivated when that state no longer holds. In one embodiment of the present teachings, the system also includes a sensor configured to detect a predetermined parameter, such as those listed herein above, and configured to provide a sensed value of the predetermined parameter to the controller component. The controller component is further configured to initiate stimulation, initiation of stimulation determined by whether the sensed value is less than or exceeds a predetermined value denoting the specific state.

Another embodiment includes method and apparatus for neuromodulatory regulation of effector organs by modulation of spinal neurons, having anode and cathode sources, having a spinal circuit for biasing a spinal electrode at a first polarity and biasing a distal reference electrode at a second polarity, and having a neural circuit for biasing a nerve associated with the muscle, the neural circuit having a charge-balancing electrode device having a first and second neural electrodes for limiting the polarizing effect of current flow in the nerve, the neural circuit biasing the first neural electrode to the second polarity and the second neural electrode at the first polarity, wherein the spinal electrode and the second neural electrode are connected to one of the sources and the first electrode is connected to the other of the sources, for activation of the effector organ of interest, as described in embodiments above.

This disclosure includes description by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hard-wired or customized circuitry to carry out logic operations that, together, perform steps of and whole processes and functionalities as described in the present disclosure.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of these teachings may be performed by a computer processor executing a program tangibly embodied on a computer-readable medium to perform functions of these teachings by operating on input and generating output.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive or external to the computing device, such as a remote memory, a disc farm or other mass storage device, etc. Commercially available microprocessors, one or more of which could be a computing device or part of a computing device, include a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices Which are well known in the art. The interconnect may include one or more buses connected to one another through various bridges, controllers and/or adapters. In one embodiment the I/O controller includes a USB (Universal Serial Bus) adapter fur controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile RAM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD RAM, a DVD or a CD), or other type of memory system which maintains data even after power is removed from the system.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

While these teachings have been described in terms of specific embodiments, it is evident in view of the foregoing description that numerous alternatives, modifications and variations will be apparent to those skilled in the art. Accordingly, these teachings are intended to encompass all such alternatives, modifications and variations which fall within the scope and spirit of the present teachings and the following claims.

The invention claimed is:

1. A system for modulation of spinal neurons associated with regulation of effector organ activity in a vertebrate being, the system comprising:
 a housing including a DC power source that provides direct current between power terminals of opposite polarity;
 a first stimulation component associated with a target effector organ including a neural stimulation circuit coupled to the terminals and having an identified neural signal output connection and an identified neural reference connection, both on said housing, and that provides a constant direct current neural stimulation signal between the identified neural signal output connection and the identified neural reference, connection for stimulation of a nerve associated with a target effector organ;
 a second stimulation component including a spinal stimulation circuit coupled to the power terminals and having an identified spinal signal output connection and an identified spinal reference connection, both on said housing, that provides a constant direct current spinal stimulation signal between the identified spinal signal connection and the identified spinal signal reference for spinal direct current stimulation associated with modulation of said target effector organ; and
 a polarity controlling component associated with the power terminals that simultaneously establishes a neural signal output connection at a first polarity and a spinal signal output connection at an opposite polarity, for stimulation of said effector organ according to the first and opposite polarities.

2. The system of claim 1 wherein the second stimulation component is configured to provide spinal non-varying continuous direct current electrical stimulation.

3. The system of claim 2 wherein the first stimulation component is configured to provide peripheral neural continuous direct current electrical stimulation.

4. The system of claim 2 wherein the first stimulation component is configured to provide non-varying continuous direct current electrical stimulation.

5. The system of claim 3 further comprising a controller component configured to simultaneously control current applied to the first and second stimulation components and to limit a current of the first component at not greater than a current at the second stimulation component.

6. The system of claim 3 further comprising a controller component configured to simultaneously control a range of current supplied by the first and second stimulation components and to establish an upper limit of current first stimulation component at not greater than a current at the second stimulation component and to dynamically adjust the upper limits simultaneously with adjustment of the current of the second stimulation component.

7. The system of claim 1, further comprising a first electrical source with positive and negative terminals configured to provide stimulation current to stimulation electrodes, disposed for stimulation of a nerve associated with a target effector organ; one electrode operatively connected to the positive terminal and another electrode operatively connected to the negative terminal; each one of said one electrode and said another electrode being electrically insulated from each other.

8. The system of claim 7 wherein said one electrode and said another electrode are configured to be attached across a section of a nerve associated with a muscle of interest to provide direct current electrical stimulation to the muscle nerve section.

9. The system of claim 8 further comprising:
 a second electrical source having a second positive terminal and a second negative terminal;
 said second electrical source configured to couple to a first electrode disposed to be placed at a spinal cord location; and
 a second reference electrode disposed to he placed at a location selected from another location at the spinal column or a location distal from the spine; one of the first electrode and the second reference electrodes being operatively connected to the second positive terminal and another one of the first electrode and the second reference electrode being operatively connected to the second negative terminal.

10. The system of claim 9 wherein the first electrical source and the second electrical source are a same electrical source; and wherein the same electrical source is a source producing non-varying direct current.

11. The system of claim 1 wherein direct current for spinal stimulation ranges from about 2 ma to about 5 mA for treatment of muscle tone in humans.

12. The system of claim 10 wherein at least one of the first electrode and the second reference electrode is implanted.

13. The system of claim 9 wherein the first electrical source is implanted; and wherein the controller component is operatively connected to the first electrical source by a wireless connection.

14. The system of claim 13 wherein the controller component is disposed in a wearable housing.

15. The system of claim 14 wherein the second electrical source is also disposed in the wearable housing.

16. The system of claim 2 wherein the first stimulation component is configured to provide pulsed electrical stimulation.

17. The system of claim 5 further comprising a sensor configured to detect a predetermined parameter and configured to provide a sensed value of the predetermined parameter to the controller component; and wherein the controller component is further configured to initiate stimulation, initiation of stimulation determined by whether the sensed value meets a criterion selected from exceeding a predetermined value or being less than the predetermined value.

18. The system of claim 3 further comprising a controller component configured to set the first of the power terminals at one polarity and the second of the power terminals at an opposite polarity.

19. The system of claim 1 further comprising:
- a controller component configured to control current applied to the first and
- second stimulation components and to limit the current at one of the first and
- second stimulation components relative to the current at one other of the first and
- second stimulation components; and
- a sensor configured to detect a predetermined parameter and configured to provide a sensed value of the predetermined parameter to the controller component;
- wherein the controller component is further configured to initiate stimulation, initiation of stimulation determined by whether the sensed value meets a criterion selected from exceeding a predetermined value or being less than the predetermined value.

20. A method for modulation of spinal neurons associated with regulation of effector organ activity in a vertebrate being, the method comprising:
- applying constant direct current from a power source to a spinal location associated with nerve associated with a target effector organ, applying a spinal neural stimulation electrode to the spinal location, and applying a spinal reference electrode distal to the spinal location, and establishing a spinal stimulation circuit between the spinal neural stimulation electrode and the spinal reference electrode;
- applying a neural stimulation electrode and neural reference electrode as an electrode set across a portion of a nerve associated with the target effector organ, and establishing a neural stimulation circuit between the neural stimulation electrode and the neural reference electrode, the neural reference electrode being distal to the spinal neural stimulation electrode and the neural stimulation electrode being proximal to the spinal neural stimulation electrode;
- applying a constant direct current spinal stimulation signal to the spinal stimulation electrode;and
- applying a constant direct current neural stimulation signal at a first polarity from the power source to the neural stimulation electrode while applying the constant direct current spinal stimulation signal to the spinal neural stimulation electrode at an opposite polarity.

21. The method of claim 20 wherein applying the direct current neural stimulation signal at a first polarity from the power source to the neural stimulation electrode while applying the direct current spinal stimulation signal to the spinal neural stimulation electrode at an opposite polarity comprises providing, from an electrical source with positive and negative terminals, stimulation current to the neural stimulation electrode and the neural reference electrode; the neural stimulation electrode operatively connected to one of the positive terminal and the negative terminal; and providing from the electrical source direct current to the spinal neural stimulation electrode at the spinal location; the spinal neural stimulation electrode being connected to a different one of the positive terminal and the negative terminal.

22. The method of claim 21 wherein the neural stimulation electrode and the neural reference electrode are located noninvasively and wherein the neural stimulation electrode and the neural reference electrode are skin-surface electrodes.

23. The method of claim 21 wherein at least one electrode is an implanted electrode.

24. The method of claim 23 wherein the electrical source is implanted.

25. The method of claim 20 wherein the spinal mural stimulation electrode and spinal reference electrode are located noninvasively and wherein the spinal neural stimulation electrode and the spinal reference electrode are skin-surface electrodes.

26. The method of claim 23 wherein the electrical source is located in a wearable housing.

27. The method of claim 26 wherein applying a direct current neural stimulation signal at a first polarity from the power source to the neural stimulation electrode while applying the direct current spinal stimulation signal to the spinal neural stimulation electrode at an opposite polarity includes delivering constant direct current to at least one of the spinal neural stimulation electrode and the neural stimulation electrode.

28. A method for modulation of spinal neurons associated with regulation of effector organ activity in a vertebrate being, comprising the steps of:
- applying a source of direct current to a portion of a nerve associated with a target effector organ,
- applying another source of direct current to a spinal location associated with said nerve associated with a target effector organ, and
- simultaneously controlling a range of current supplied to each of said nerve portion and spinal location for establishing the upper limit of said peripheral current at not greater than said spinal current;
- wherein establishing the upper limit includes dynamically adjusting the upper limit simultaneously with adjustment of the spinal current.

29. A system for modulation of spinal neurons associated with regulation of effector organ activity in a vertebrate being, the system comprising:
- a first stimulation component configured to provide stimulation of a nerve associated with a target effector organ,
- a second stimulation component configured to provide spinal direct current stimulation associated with modulation of the target effector organ, and
- a controller component configured to simultaneously control a range of current supplied by the first and second stimulation components and establishing an upper limit of current of the first stimulation component at not greater than a current at the second stimulation component and dynamically adjusting the upper limit simultaneously with adjustment of the current at the second stimulation component;
wherein the second stimulation component is configured to provide spinal non-varying continuous direct current electrical stimulation; and
wherein the first stimulation component is configured to provide direct current electrical stimulation.

* * * * *

UNITED STATES PATENT AND TRADEMARK OFFICE
CERTIFICATE OF CORRECTION

| | | |
|---|---|---|
| PATENT NO. | : 9,283,391 B2 | Page 1 of 1 |
| APPLICATION NO. | : 14/579829 | |
| DATED | : March 15, 2016 | |
| INVENTOR(S) | : Zaghloul Ahmed | |

It is certified that error appears in the above-identified patent and that said Letters Patent is hereby corrected as shown below:

Claims

In column 27, line 53 (claim 1), "neural reference, connection" should read -- neural reference connection --

In column 28, line 47 (claim 9), "disposed to he placed" should read -- disposed to be placed --

In column 28, line 50 (claim 9), "second reference electrodes" should read -- second reference electrode --

In column 30, lines 24-25 (claim 25), "spinal mural stimulation electrode" should read -- spinal neural stimulation electrode --

Signed and Sealed this
Seventeenth Day of May, 2016

Michelle K. Lee
*Director of the United States Patent and Trademark Office*